US008530233B2

(12) United States Patent
Lin

(10) Patent No.: US 8,530,233 B2
(45) Date of Patent: Sep. 10, 2013

(54) EXPRESSION VECTOR WITH ENHANCED GENE EXPRESSION CAPACITY AND METHOD FOR USING THE SAME

(75) Inventor: Ching-Tai Lin, Sanchong (TW)

(73) Assignee: Genetai Inc, Ebene (MU)

( * ) Notice: Subject to any disclaimer, the term of this patent is extended or adjusted under 35 U.S.C. 154(b) by 1177 days.

(21) Appl. No.: 11/905,618

(22) Filed: Oct. 2, 2007

(65) Prior Publication Data

US 2009/0087883 A1      Apr. 2, 2009

(51) Int. Cl.
*C12N 15/00* (2006.01)
*C12P 21/06* (2006.01)
*C12P 21/04* (2006.01)
*C12N 5/02* (2006.01)
*C12N 5/10* (2006.01)
*C12N 5/071* (2010.01)

(52) U.S. Cl.
USPC ..... 435/320.1; 435/69.1; 435/70.1; 435/70.3; 435/325; 435/358; 435/366

(58) Field of Classification Search
None
See application file for complete search history.

(56) References Cited

FOREIGN PATENT DOCUMENTS

| WO | WO 2005/056750 | 6/2005 |
|---|---|---|
| WO | WO 2007/048601 | 5/2007 |
| WO | WO 2007/150036 | 12/2007 |

OTHER PUBLICATIONS

Xin Bi et al, "DNA Rearrangement Medicated by Inverted Repeats", Proc. Natl. Acad. Sci. USA, vol. 93, 1996, pp 819-823.

Ching-Tai Lin et al., "A Cruciform-Dumbbell Model for Inverted Dimer Formation Mediated by Inverted Repeats", Nucleic Acids Research, vol. 25, No. 15, 1997, pp. 3009-3016.

Ching-Tai Lin et al., "Suppression of Gene Amplification and Chromosomal DNA Integration by the DNA Mismatch Repair System", Nucleic Acids Research, vol. 29, No. 16, 2001, pp. 3304-3310.

Sihong Chen et al., "High Rate of CAD Gene Amplification In Human Cells Deficient in MLH1 or MSH6", PNAS, vol. 98, No. 24, Nov. 2001, pp. 13802-13807.

Vidhya Narayanan et al, "The Pattern of Gene Amplification Is Determined by the Chromosomal Location of Hairpin-Capped Breaks", Cell 125, 2006 Elsevier Inc., Jun. 30, 2006, pp. 1283-1296.

James E. Haber et al., "Gene Amplification: Yeast Takes A Turn", Cell 125, Jun. 30, 2006, 2006 Elseview Inc., pp. 1237-1240.

Rajkumar Kunaparaju et al., "Epi-CHO, An Episomal Expression System for Recombinant Protein Production in CHO Cells", Biotechnology and Bioengineering, vol. 91, No. 6, Sep. 20, 2005, pp. 670-677.

Hisashi Tanaka et al., " Short Inverted Repeats Initiate Gene Amplification Through the Formation of a Large DNA Palindrome in Mammalian Cells" PNAS, vol. 99, No. 13, Jun. 25, 2002, pp. 8772-8777.

Ching-Tai Lin et al., "Inverted Repeats as Genetic Elements for Promoting DNA Inverted Duplication: Implications in Gene Amplification", Nucleic Acids Research, vol. 29, No. 17, 2001, pp. 3529-3538.

International Search Report of EP 08013502.3-2403, Nov. 19, 2008.

*Primary Examiner* — Anne Gussow
*Assistant Examiner* — Nancy J Leith
(74) *Attorney, Agent, or Firm* — Aldo Noto; Michael Ye; Andrews Kurth, LLP

(57) ABSTRACT

The present invention provides a novel expression vector which comprises a gene of interest, a nuclear anchoring element, and at least one inverted repeat element, preferably two inverted repeat elements. The expression vector is an episomal vector capable of transfecting a mammalian cell. The present invention further provides a method for enhancing gene expression by transfecting the expression vector to a mammalian cell, preferably a human cell.

27 Claims, 10 Drawing Sheets

DLD-1 cells + pGT04/ID

SEQUENCE LISTING

```
<160> NUMBER OF SEQ ID NOS: 2

<210> SEQ ID NO 1
<211> LENGTH: 20
<212> TYPE: DNA
<213> ORGANISM: artificial
<220> FEATURE:
<223> OTHER INFORMATION: synthetic sequence
```

-continued

<400> SEQUENCE: 1
taatccggat ttccggatta                                                        20

<210> SEQ ID NO 2
<211> LENGTH: 27021
<212> TYPE: DNA
<213> ORGANISM: artificial
<220> FEATURE:
<223> OTHER INFORMATION: plasmid sequence

<400> SEQUENCE: 2
cgaacgccag caagacgtag cccagcgcgt cggccgccat gccggcgata atggcctgct       60
tctcgccgaa acgtttggtg gcgggaccag tgacgaaggc ttgagcgagg gcgtgcaaga      120
ttccgaatac cgcaagcgac aggccgatca tcgtcgcgct ccagcgaaag cggtcctcgc      180
cgaaaatgac ccagagcgct gccggcacct gtcctacgag ttgcatgata aagaagacag      240
tcataagtgc ggcgacgata gtcatgcccc gcgcccaccg gaaggagctg actgggttga      300
aggctctcaa gggcatcggt cgacgctctc ccttatgcga ctcctgcatt aggaagcagc      360
ccagtagtag gttgaggccg ttgagcaccg ccgccgcaag gaatggtgca tgcaaggaga      420
tggcgcccaa cagtcccccg gccacggggc ctgccaccat acccacgccg aaacaagcgc      480
tcatgagccc gaagtggcga gcccgatctt ccccatcggt gatgtcggcg atataggcgc      540
cagcaaccgc acctgtggcg ccggtgatgc cggccacgat gcgtccggcg tagaggatcc      600
acaggacggg tgtggtcgcc atgatcgcgt agtcgatagt ggctccaagt agcgaagcga      660
gcaggactgg gcggcggcca aagcggtcgg acagtgctcc gagaacgggt gcgcatagaa      720
attgcatcaa cgcatatagc gctagcagca cgccatagtg actggcgatg ctgtcggaat      780
ggacgatatc ccgcaagagg cccggcagta ccggcataac caagcctatg cctacagcat      840
ccagggtgac ggtgccgagg atgacgatga gcgcattgtt agatttcata cacggtgcct      900
gactgcgtta gcaatttaac tgtgataaac taccgcatta aagcttatcg atgataagct      960
gtcaaacatg agaatcgacc gatgcccttg agagccttca acccagtcag ctccttccgg     1020
tgggcgcggg gcatgactat cgtcgccgca cttatgactg tcttctttat catgcaactc     1080
gtaggacagg tgccggcagc gctctgggtc attttcggcg aggaccgctt tcgctggagc     1140
gcgacgatga tcggcctgtc gcttgcggta ttcggaatct tgcacgccct cgctcaagcc     1200
ttcgtcactg gtcccgccac caaacgtttc ggcgagaagc aggccattat cgccggcatg     1260
gcggccgacg cgctgggcta cgtcttgctg gcgttcggat cccccgccgc cggacgaact     1320
aaacctgact acggcatctc tgcccccttct tcgctggtac gaggagcgct tttgttttgt     1380
attggtcacg gggcagtgca tgtaatccct tcagttggtt ggtacaactt gccaactggg     1440
ccctgttcca catgtgacac ggggggggac caaacacaaa ggggttctct gactgtagtt     1500
gacatcctta taaatggatg tgcacatttg ccaacactga gtggctttca tcctggagca     1560
gactttgcag tctgtggact gcaacacaac attgccttta tgtgtaactc ttggctgaag     1620
ctcttacacc aatgctgggg gacatgtacc tcccaggggc ccaggaagac tacgggaggc     1680
tacaccaacg tcaatcagag gggcctgtgt agctaccgat aagcggaccc tcaagagggc     1740
attagcaata gtgtttataa ggccccttg ttaaccctaa cgggtagca tatgcttccc     1800
gggtagtagt atatactatc cagactaacc ctaattcaat agcatatgtt acccaacggg     1860
aagcatatgc tatcgaatta gggttagtaa aagggtccta aggaacagcg atatctccca     1920
ccccatgagc tgtcacggtt ttatttacat ggggtcagga ttccacgagg gtagtgaacc     1980

```
attttagtca caagggcagt ggctgaagat caaggagcgg gcagtgaact ctcctgaatc    2040
ttcgcctgct tcttcattct ccttcgttta gctaatagaa taactgctga gttgtgaaca    2100
gtaaggtgta tgtgaggtgc tcgaaaacaa ggtttcaggt gacgccccca gaataaaatt    2160
tggacggggg gttcagtggt ggcattgtgc tatgacacca atataaccct cacaaacccc    2220
ttgggcaata atactagtg taggaatgaa acattctgaa tatctttaac aatagaaatc    2280
catggggtgg ggacaagccg taaagactgg atgtccatct cacacgaatt tatggctatg    2340
ggcaacacat aatcctagtg caatatgata ctggggttat taagatgtgt cccaggcagg    2400
gaccaagaca ggtgaaccat gttgttacac tctatttgta acaaggggaa agagagtgga    2460
cgccgacagc agcggactcc actggttgtc tctaacaccc ccgaaaatta acgggggctc    2520
cacgccaatg gggcccataa acaaagacaa gtggccactc ttttttttga aattgtggag    2580
tgggggcacg cgtcagcccc cacacgccgc cctgcggttt tggactgtaa ataagggtg    2640 taataacttg gctgattgta accccgctaa ccactgcgt caaaccactt gcccacaaaa    2700
ccactaatgg caccccgggg aatacctgca taagtaggtg ggcgggccaa gatagggcg    2760 cgattgctgc gatctggagg acaaattaca cacacttgcg cctgagcgcc aagcacaggg    2820
ttgttggtcc tcatattcac gaggtcgctg agagcacggt gggctaatgt tgccatgggt    2880
agcatatact acccaaaatat ctggatagca atgctatcc taatctatat ctgggtagca    2940
taggctatcc taatctatat ctgggtagca tatgctatcc taatctatat ctgggtagta    3000
tatgctatcc taatttatat ctgggtagca taggctatcc taatctatat ctgggtagca    3060
tatgctatcc taatctatat ctgggtagta tatgctatcc taatctgtat ccgggtagca    3120
tatgctatcc taatagagat tagggtagta tatgctatcc taattatat ctgggtagca    3180 tatactaccc aaatatctgg atagcatatg ctatcctaat ctatatctgg gtagcatatg    3240
ctatcctaat ctatatctgg gtagcatagg ctatcctaat ctatatctgg gtagcatatg    3300
ctatcctaat ctatatctgg gtagtatatg ctatcctaat ttatatctgg gtagcatagg    3360
ctatcctaat ctatatctgg gtagcatatg ctatcctaat ctatatctgg gtagtatatg    3420
ctatcctaat ctgtatccgg gtagcatatg ctatcctcat gcatatacag tcagcatatg    3480
atacccagta gtagagtggg agtgctatcc tttgcatatg ccgccacctc ccaaggggggc    3540 gtgaattttc gctgcttgtc cttttcctgc tggttgctcc cattcttagg tgaatttaag    3600
gaggccaggc taaagccgtc gcatgtctga ttgctcacca ggtaaatgtc gctaatgttt    3660
tccaacgcga gaaggtgttg agcgcggagc tgagtgacgt gacaacatgg gtatgcccaa    3720
ttgccccatg ttgggaggac gaaaatggtg acaagacaga tggccagaaa tacaccaaca    3780
gcacgcatga tgtctactgg ggatttattc tttagtgcgg gggaatacac ggcttttaat    3840
acgattgagg gcgtctccta acaagttaca tcactcctgc ccttcctcac cctcatctcc    3900
atcacctcct tcatctccgt catctccgtc atcaccctcc gcggcagccc cttccaccat    3960
aggtggaaac cagggaggca aatctactcc atcgtcaaag ctgcacacag tcaccctgat    4020
attgcaggta ggagcgggct tgtcataac aaggtcctta atcgcatcct tcaaaacctc    4080
agcaaatata tgagtttgta aaagaccat gaaataacag acaatggact cccttagcgg    4140
gccaggttgt gggccgggtc caggggccat tccaagggg agacgactca atggtgtaag    4200
acgacattgt ggaatagcaa gggcagttcc tcgccttagg ttgtaaaggg aggtcttact    4260
acctccatat acgaacacac cggcgaccca agttccttcg tcggtagtcc tttctacgtg    4320
actcctagcc aggagagctc ttaaaccttc tgcaatgttc tcaaatttcg ggttggaacc    4380
```

```
tccttgacca cgatgctttc caaaccaccc tccttttttg cgcctgcctc catcaccctg    4440
accccggggt ccagtgcttg ggccttctcc tgggtcatct gcggggccct gctctatcgc    4500
tcccgggggc acgtcaggct caccatctgg gccaccttct tggtggtatt caaaataatc    4560
ggcttcccct acagggtgga aaaatggcct tctacctgga gggggcctgc gcggtggaga    4620
cccggatgat gatgactgac tactgggact cctgggcctc ttttctccac gtccacgacc    4680 tctcccctg gctcttcac gacttccccc cctggctctt tcacgtcctc taccccggcg     4740
gcctccacta cctcctcgac cccggcctc actacctcct cgaccccggc tccactgcc     4800 tcctcgaccc cggcctccac ctcctgctcc tgccctcct gctcctgccc ctcctcctgc    4860
tcctgcccct cctgcccctc ctgctcctgc cctcctgcc cctcctgctc ctgcccctcc    4920
tgcccctcct gctcctgccc ctcctgcccc tcctcctgct cctgcccctc ctgcccctcc    4980
tcctgctcct gccctcctg cccctcctgc tcctgccct ctgcccctc ctgctcctgc      5040 ccctcctgcc cctcctgctc ctgcccctcc tgctcctgcc cctcctgctc ctgcccctcc    5100
tgctcctgcc cctcctgccc ctgcccctc tcctgcct cctgcccctc ctgctcctgc      5160
ccctcctgcc cctcctgccc ctcctgctcc tgccctcct cctgctcctg cccctcctgc    5220
ccctcctgcc cctcctcctg ctcctgcccc tcctgcccct cctgctcctc ctgcccctcc    5280
tcctgctcct gccctcctg cccctcctgc cctcctcct gctcctgccc ctcctgcccc    5340
tcctcctgct cctgcccctc ctgctcctgc tgccctcct gcccctcctg ccctccctcc    5400
tgctcctgcc cctcctcctg ctcctgcccc tcctgccct cctgcccctc ctgcccctcc    5460
tcctgctcct gccctcctc ctgctcctgc cctcctgct cctgccctc cgctcctgc       5520 tcctgctcct gttccaccgt gggtcccttt gcagccaatg caacttggac gtttttgggg    5580
tctccggaca ccatctctat gtcttggccc tgatcctgag ccgcccgggg ctcctggtct    5640
tccgcctcct cgtcctcgtc ctcttcccg tcctcgtcca tggttatcac ccctcttct     5700 ttgaggtcca ctgccgccgg agccttctgg tccagatgtg tctcccttct ctcctaggcc    5760
atttccaggt cctgtacctg gccctcgtc agacatgatt cacactaaaa gagatcaata    5820
gacatcttta ttagacgacg ctcagtgaat acagggagtg cagactcctg cccctccaa     5880 cagccccccc accctcatcc ccttcatggt cgctgtcaga cagatccagg tctgaaaatt    5940
ccccatcctc cgaaccatcc tcgtcctcat caccaattac tcgcagcccg gaaaactccc    6000
gctgaacatc ctcaagattt gcgtcctgag cctcaagcca ggcctcaaat tcctcgtccc    6060 ccttttttgct ggacggtagg gatggggatt ctcgggaccc ctcctcttcc tcttcaaggt    6120
caccagacag agatgctact ggggcaacgg aagaaaagct gggtgcggcc tgtgaggatc    6180
agcttatcga tgataagctg tcaaacatga gaattcttga agacgaaagg gcctcgtgat    6240
acgcctattt ttataggtta atgtcatgat aataatggtt tcttagacgt caggtggcac    6300
ttttcgggga aatgtgcgcg gaaccctat ttgtttattt ttctaaatac attcaaatat      6360
gtatccgctc atgagacaat aaccctgata atgcttcaa taatattgaa aaaggaagag    6420
tatgagtatt caacatttcc gtgtcgccct tattcccttt tttgcggcat tttgccttcc    6480 tgttttttgct cacccagaaa cgctggtgaa agtaaaagat gctgaagatc agttgggtgc    6540
acgagtgggt tacatcgaac tggatctcaa cagcggtaag atccttgaga gttttcgccc    6600
cgaagaacgt tttccaatga tgagcacttt taaagttctg ctatgtggcg cggtattatc    6660
ccgtgttgac gccgggcaag agcaactcgg tcgccgcata cactattctc agaatgactt    6720
ggttgagtac tcaccagtca cagaaaagca tcttacggat ggcatgacag taagagaatt    6780
```

```
atgcagtgct gccataacca tgagtgataa cactgcggcc aacttacttc tgacaacgat    6840
cggaggaccg aaggagctaa ccgcttttt  gcacaacatg ggggatcatg taactcgcct    6900
tgatcgttgg gaaccggagc tgaatgaagc cataccaaac gacgagcgtg acaccacgat    6960
gcctgcagca atggcaacaa cgttgcgcaa actattaact ggcgaactac ttactctagc    7020
ttcccggcaa caattaatag actggatgga ggcggataaa gttgcaggac cacttctgcg    7080
ctcggccctt ccggctggct ggtttattgc tgataaatct ggagccggtg agcgtgggtc    7140
tcgcggtatc attgcagcac tggggccaga tggtaagccc tcccgtatcg tagttatcta    7200
cacgacgggg agtcaggcaa ctatggatga acgaaataga cagatcgctg ataggtgc     7260
ctcactgatt aagcattggt aactgtcaga ccaagtttac tcatatatac tttagattga    7320
tttaaaactt catttttaat ttaaaaggat ctaggtgaag atcctttttg ataatctcat    7380
gaccaaaatc ccttaacgtg agttttcgtt ccactgagcg tcagacccg  tagaaaagat    7440
caaaggatct tcttgagatc cttttttct  gcgcgtaatc tgctgcttgc aaacaaaaaa    7500
accaccgcta ccagcggtgg tttgtttgcc ggatcaagag ctaccaactc tttttccgaa    7560
ggtaactggc ttcagcagag cgcagatacc aaatactgtc cttctagtgt agccgtagtt    7620
aggccaccac ttcaagaact ctgtagcacc gcctacatac ctcgctctgc taatcctgtt    7680
accagtggct gctgccagtg gcgataagtc gtgtcttacc gggttggact caagacgata    7740
gttaccggat aaggcgcagc ggtcgggctg aacggggggt tcgtgcacac agcccagctt    7800
ggagcgaacg acctacaccg aactgagata cctacagcgt gagctatgag aaagcgccac    7860
gcttcccgaa gggagaaagg cggacaggta ccggtaagc  ggcagggtcg aacaggaga     7920
gcgcacgagg gagcttccag ggggaaacgc ctggtatctt tatagtcctg tcgggtttcg    7980
ccacctctga cttgagcgtc gatttttgtg atgctcgtca gggggggcgga gcctatggaa    8040
aaacgccagc aacgcggcct ttttacggtt cctggccttt tgctggcgct ggtaagagcc    8100
gcgagcgatc cttgaagctg tccctgatgg tcgtcatcta cctgcctgga cagcatggcc    8160
tgcaacgcgg gcatcccgat gccgccggaa gcgagaagaa tcataatggg gaaggccatc    8220
cagcctcgcg tcgcgaacgc cagcaagacg tagcccagcg cgtcggcccc gagatgcgcc    8280
gcgtgcggct gctggagatg gcggacgcga tggatatgtt ctgccaaggg ttggtttgcg    8340
cattcacagt tctccgcaag aattgattgg ctccaattct tggagtggtg aatccgttag    8400
cgaggtgccg ccgggctgct tcatcccgt  ggcccgttgc tcgcgtttgc tggcggtgtc    8460
cccggaagaa atatatttgc atgtctttag ttctatgatg acacaaaccc cgcccagcgt    8520
cttgtcattg gcgaattcga acacgcagat gcagtcgggg cggcgcggtc ccaggtccac    8580
ttcgcatatt aaggtgacgc gtgtggcctc gaacaccgag cgaccctgca gcgacccgct    8640
taacagcgtc aacagcgtgc cgcaagatcc ccggggcaa  tgagatatga aaaagcctga    8700
actcaccgcg acgtctgtcg agaagtttct gatcgaaaag ttcgacagcg tctccgacct    8760
gatgcagctc tcggagggcg aagaatctcg tgctttcagc ttcgatgtag gagggcgtgg    8820
atatgtcctg cgggtaaata gctgcgccga tggtttctac aaagatcgtt atgtttatcg    8880
gcactttgca tcggccgcgc tcccgattcc ggaagtgctt gacattgggg aattcagcga    8940
gagcctgacc tattgcatct cccgccgtgc acagggtgtc acgttgcaag acctgcctga    9000
aaccgaactg cccgctgttc tgcagccggt cgcggaggcc atggatgcga tcgctgcggc    9060
cgatcttagc cagacgagcg gttcggccc  attcggaccg caaggaatcg gtcaatacac    9120
tacatggcgt gatttcatat gcgcgattgc tgatccccat gtgtatcact ggcaaactgt    9180
```

-continued

```
gatggacgac accgtcagtg cgtccgtcgc gcaggctctc gatgagctga tgctttgggc    9240
cgaggactgc cccgaagtcc ggcacctcgt gcacgcggat ttcggctcca acaatgtcct    9300
gacggacaat ggccgcataa cagcggtcat tgactggagc gaggcgatgt tcggggattc    9360
ccaatacgag gtcgccaaca tcttcttctg gaggccgtgg ttggcttgta tggagcagca    9420
gacgcgctac ttcgagcgga ggcatccgga gcttgcagga tcgccgcggc tccgggcgta    9480
tatgctccgc attggtcttg accaactcta tcagagcttg gttgacggca atttcgatga    9540
tgcagcttgg gcgcagggtc gatgcgacgc aatcgtccga tccggagccg ggactgtcgg    9600
gcgtacacaa atcgcccgca gaagcgcggc cgtctggacc gatggctgtg tagaagtact    9660
cgccgatagt ggaaaccgac gccccagcac tcgtggggat cgggagatgg gggaggctaa    9720
ctgaaacacg gaaggagaca ataccggaag gaacccgcgc tatgacggca ataaaaagac    9780
agaataaaac gcacgggtgt tgggtcgttt gttcataaac gcggggttcg gtcccagggc    9840
tggcactctg tcgataccccc accgagaccc cattggggcc aatacgcccg cgtttcttcc    9900
ttttccccac cccaaccccc aagttcgggt gaaggcccag ggctcgcagc caacgtcggg    9960
gcggcaagcc cgccatagcc acgggccccg tgggttaggg acggggtccc ccatggggaa   10020
tggtttatgg ttcgtggggg ttattctttt gggcgttgcg tggggtcagg tccacgactg   10080
gactgagcag acagacccat ggttttttgga tggcctgggc atggaccgca tgtactggcg   10140
cgacacgaac accgggcgtc tgtggctgcc aaacacccccc gaccccccaaa aaccaccgcg   10200 cggatttctg gcgccagtgc caagcttggg cagaaatggt tgaactcccg agagtgtcct   10260
acacctaggg gagaagcagc caaggggttg tttcccacca aggacgaccc gtctgcgcac   10320
aaacggatga gcccatcaga caaagacata ttcattctct gctgcaaact tggcatagct   10380
ctgctttgcc tggggctatt ggggggaagtt gcggttcgtg ctcgcagggc tctcacccctt   10440 gactctttta atagctcttc tgtgcaagat tacaatctaa acaattcgga gaactcgacc   10500
ttcctcctga ggcaaggacc acagccaact tcctcttaca agccgcatcg attttgtcct   10560
tcagaaatag aaataagaat gcttgctaaa aattatattt ttaccaataa gaccaatcca   10620
ataggtagat tattagttac tatgttaaga aatgaatcat tatcttttag tactattttt   10680
actcaaattc agaagttaga aatgggaata gaaaatagaa agagacgctc aacctcaatt   10740
gaagaacagg tgcaaggact attgaccaca ggcctagaag taaaaaggg aaaaaagagt   10800 gttttttgtca aaataggaga caggtggtgg caaccaggga cttataggggg accttacatc   10860 tacagaccaa cagatgccccc cttaccatat acaggaagat atgacttaaa ttgggatagg   10920
tgggttacag tcaatggcta taaagtgtta tatagatccc tccctttttcg tgaaagactc   10980 gccagagcta gacctccttg gtgtatgttg tctcaagaag aaaaagacga catgaaacaa   11040
caggtacatg attatattta tctaggaaca ggaatgcact tttggggaaa gattttccat   11100
accaaggagg ggacagtggc tggactaata gaacattatt ctgcaaaaac tcatggcatg   11160
agttattatg aatagccttt attgcccaa ccttgcggtt cccagggctt aacacgtgtg   11220
tcgggtcgaa cctcgcttgc tggatgtggc ttgactctat ggatgtcgca ctcgatactc   11280
tttcgcggtg cgaagggctt ccctcttttcc gcctgtccat aggccattcg ccgtcccagc   11340
cttgtcctct cgcgtgctcc ctcgaaggtc ccccttttgcg gaccatagaa atatcaggac   11400
agcccaaagc ggtggagact gaactcgcag ctaaaaacac tacgagcagt ccccccgcct   11460
cggatacctt tttgcggtcg ttgcgccgga aaaatgccaa ggaccggaaa acgaccgaa   11520 aacgagtgta caagaaagga cgcaataggg gactaagaca cctattggca taatggcggt   11580
```

```
acgtaatcaa taattatcat tagttaatgc cccagtaatc aagtatcggg tatatacctc   11640
aaggcgcaat gtattgaatg ccatttaccg ggcggaccga ctggcgggtt gctgggggcg   11700
ggtaactgca gttattactg catacaaggg tatcattgcg gttatccctg aaaggtaact   11760
gcagttaccc acctcataaa tgccatttga cgggtgaacc gtcatgtagt tcacatagta   11820
tacggttcat gcgggggata actgcagtta ctgccattta ccgggcggac cgtaatacgg   11880
gtcatgtact ggaataccct gaaaggatga accgtcatgt agatgcataa tcagtagcga   11940
taatggtacc actacgccaa aaccgtcatg tagttacccg cacctatcgc caaactgagt   12000 gccctaaag gttcagaggt ggggtaactg cagttaccct caaacaaaac cgtggtttta   12060
gttgccctga aaggttttac agcattgttg aggcggggta actgcgttta cccgccatcc   12120
gcacatgcca ccctccagat atattcgtct cgaccaaatc acttggcagt ctaggcgatc   12180
gcgatggcct gagtctaggt ggccagcggt ggtaccactc gttcccgctc ctcgacaagt   12240
ggccccacca cgggtaggac cagctcgacc tgccgctgca tttgccggtg ttcaagtcgc   12300
acaggccgct cccgctcccg ctacggtgga tgccgttcga ctgggacttc aagtagacgt   12360
ggtggccgtt cgacgggcac gggacccggt gggagcactg gtgggactgg atgccgcacg   12420
tcacgaagtc ggcgatgggg ctggtgtact tcgtcgtgct gaagaagttc aggcggtacg   12480
ggcttccgat gcaggtcctc gcgtggtaga agaagttcct gctgccgttg atgttctggg   12540
cgcggctcca cttcaagctc ccgctgtggg accacttggc gtagctcgac ttcccgtagc   12600
tgaagttcct cctgccgttg taggaccccg tgttcgacct catgttgatg ttgtcggtgt   12660
tgcagatata gtaccggctg ttcgtcttct tgccgtagtt ccacttgaag ttctaggcgg   12720
tgttgtagct cctgccgtcg cacgtcgagc ggctggtgat ggtcgtcttg tgggggtagc   12780
cgctgccggg gcacgacgac gggctgttgg tgatggactc gtgggtcagg cgggactcgt   12840 ttctgggggtt gctcttcgcg ctagtgtacc aggacgacct caagcactgg cggcggccct   12900
agtgagagcc gtacctgctc gacatgttca tttcgccggc gctgagatct agtattagtc   12960
ggtatggtgt aaacatctcc aaaatgaacg aaattttttg gagggtgtgg aggggggactt   13020 ggactttgta ttttacttac gttaacaaca acaattgaac aaataacgtc gaatattacc   13080
aatgtttatt tcgttatcgt agtgtttaaa gtgtttattt cgtaaaaaaa gtgacgtaag   13140
atcaacacca aacaggtttg agtagttaca tagaatttta agtaagtttt tggttacaaa   13200
ctgttcttaa aacgaggatg tgagacaagt ggtttcctga cttggtttgg tatcaaaggt   13260
tctgatctga gctctgagtg ttctattttc ctatgttctt ttggaattta tccaaatctt   13320
atgtaaatgc ttatgtaaac caagatataa aagagtgctg attttttgag taaacttgca   13380
acagtcctaa cattcacctc ttgtgtgttt gtgtctgttc gccatcccgt ctccgctcgt   13440
cacttatcct tcactttcca gagggtcccc ccgcagaccc cggcgaccct caggtcggcc   13500
gactgcggca gcgaacgcca gcaagacgta gcccagcgcg tcgccgcca tgccggcgat   13560 aatggcctgc ttctcgccga aacgtttggt ggcgggacca gtgacgaagg cttgagcgag   13620
ggcgtgcaag attccgaata ccgcaagcga caggccgatc atcgtcgcgc tccagcgaaa   13680
gcggtcctcg ccgaaaatga cccagagcgc tgccggcacc tgtcctacga gttgcatgat   13740
aaagaagaca gtcataagtg cggcgacgat agtcatgccc cgcgcccacc ggaaggagct   13800
gactgggttg aaggctctca agggcatcgg tcgattctca tgtttgacag cttatcatcg   13860
ataagcttta atgcggtagt ttatcacagt taaattgcta acgcagtcag gcaccgtgta   13920
tgaaatctaa caatgcgctc atcgtcatcc tcggcaccgt caccctggat gctgtaggca   13980
```

```
taggcttggt tatgccggta ctgccgggcc tcttgcggga tatcgtccat tccgacagca   14040
tcgccagtca ctatggcgtg ctgctagcgc tatatgcgtt gatgcaattt ctatgcgcac   14100
ccgttctcgg agcactgtcc gaccgctttg gccgccgccc agtcctgctc gcttcgctac   14160
ttggagccac tatcgactac gcgatcatgg cgaccacacc cgtcctgtgg atcctctacg   14220
ccggacgcat cgtggccggc atcaccggcg ccacaggtgc ggttgctggc gcctatatcg   14280
ccgacatcac cgatggggaa gatcgggctc gccacttcgg gctcatgagc gcttgtttcg   14340
gcgtgggtat ggtggcaggc cccgtggccg ggggactgtt gggcgccatc tccttgcatg   14400
caccattcct tgcggcggcg gtgctcaacg gcctcaacct actactgggc tgcttcctaa   14460
tgcaggagtc gcataaggga gagcgtcgac cgatgcccct tgagagcctt caacccagtca  14520 gctccttccg gtgggcgcgg ggcatgacta tcgtcgccgc acttatgact gtcttctttta  14580 tcatgcaact cgtaggacag gtgccggcag cgctctgggt cattttcggc gaggaccgct   14640
ttcgctggag cgcgacgatg atcggcctgt cgcttgcggt attcggaatc ttgcacgccc   14700
tcgctcaagc cttcgtcact ggtcccgcca ccaaacgttt cggcgagaag caggccatta   14760
tcgccggcat ggcggccgac gcgctgggct acgtcttgct ggcgttcgtg ccgcagtcgg   14820
ccgacctgag ggtcgccggg gtctgcgggg ggaccctctg gaaagtgaag gataagtgac   14880
gagcggagac gggatggcga acagacacaa acacacaaga ggtgaatgtt aggactgttg   14940
caagtttact caaaaaatca gcactctttt atatcttggt ttacataagc atttacataa   15000
gatttggata aattccaaaa gaacatagga aaatagaaca ctcagagctc agatcagaac   15060
ctttgatacc aaaccaagtc aggaaaccac ttgtctcaca tcctcgtttt aagaacagtt   15120
tgtaaccaaa aacttactta aaattctatg taactactca aacctgtttg gtgttgatct   15180
tacgtcactt tttttacgaa ataaacactt taaacactac gataacgaaa taaacattgg   15240
taatattcga cgttatttgt tcaattgttg ttgttaacgt aagtaaaata caaagtccaa   15300 gtcccctcc acaccctcca aaaaatttcg ttcattttgg agatgtttac accataccga   15360
ctaatactag atctcagcgc cggcgaaatg aacatgtcga gcaggtacgg ctctcactag   15420
ggccgccgcc agtgcttgag gtcgtcctgg tacactagcg cgaagagcaa ccccagaaac   15480
gagtcccgcc tgaccacgca gtccatcacc aacagcccgt cgtcgtgccc cggcagcggc   15540 taccccaca agacgaccat caccagccgc tcgacgtgcg acggcaggag ctacaacacc   15600
gcctagaact tcaagtggaa ctacggcaag aagacgaaca gccggtacta tatctgcaac   15660
accgacaaca tcaacatgag gtcgaacacg gggtcctaca acggcaggag gaacttcagc   15720
tacgggaagt cgagctacgc caagtggtcc cacagcggga gcttgaagtg gagccgcgcc   15780
cagaacatca acggcagcag gaacttcttc taccacgcga ggacctgcat cggaagcccg   15840
taccgcctga acttcttcag cacgacgaag tacaccagcc ccatcgccga cttcgtgacg   15900
tgcggcatcc agtcccacca gtgctcccac ccggtcccgt gccgtcgaa cggccaccac   15960 gtctacttga agtcccagtc gaacggcatc caccgtagcg ggagcggag cggcctgtgc   16020 gacttgaaca ccggcaaatg cagcggcagg tcgagctggt cctacccgtg gtggggccac   16080
ttgtcgagga gcgggaacga gtggtaccac cgctggccac ctagactcag gccatcgcga   16140
tcgcctagac tgccaagtga tttggtcgag acgaatatat ctggagggtg gcatgtgcgg   16200
atggcgggta aacgcagtta ccccgcctca acaatgctgt aaaacctttc agggcaacta   16260
aaaccacggt tttgtttgag ggtaactgca gttaccccac ctctgaacct ttaggggcac   16320
tcagtttggc gataggtgcg ggtaactaca tgacggtttt ggcgtagtgg taccattatc   16380
```

```
gctactgatt atgcatctac atgacggttc atcctttcag ggtattccag tacatgaccc    16440
gtattacggt ccgcccggta aatggcagta actgcagtta tccccgcat gaaccgtata     16500
ctatgtgaac tacatgacgg ttcacccgtc aaatggcatt tatgaggtgg gtaactgcag    16560
ttacctttca gggataaccg caatgatacc cttgtatgca gtaataactg cagttacccg    16620
cccccagcaa cccgccagtc ggtccgcccg gtaaatggca ttcaatacat tgcgccttga    16680
ggtatatacc cgatacttga ttactggggc attaactaat gataattatt gattacgtac    16740
cgccattatg ccaataggtg tcttagtccc ctattgcgtc ctttcttgta cactcgtttt    16800
ccggtcgttt tccggtcctt ggcatttttc cggcgcaacg accgcaaaaa ggtatccgag    16860
gcgggggggac tgctcgtagt gttttttagct gcgagttcag tctccaccgc tttgggctgt  16920
cctgatattt ctatggtccg caaagggga ccttcgaggg agcacgcgag aggacaaggc     16980
tgggacggcg aatggcctat ggacaggcgg aaagagggaa gcccttcgca ccgcgaaaga    17040
gtatcgagtg cgacatccat agagtcaagc cacatccagc aagcgaggtt cgacccgaca    17100
cacgtgttaa gccctgggaa ccgcaaggtt gggccaataa aggctattca taataactca    17160
tgccatgagt ttttgcagaa taatgttcta ttagtccagc cactgtcccc tccttggtat    17220
ggaaaatctt tccccaaaag tgcattcctg ttcctagata aatataatca tgtacctgtt    17280
gtttcatgtc gtcttttctt tcttgagaca acatacacca aggaggtcta gctctgcgca    17340
gtctttcacg aaaagggagg gatctatata acactttata gccattgact gtaacccacc    17400
tatcccaatt taagtcatat cttcctgtat atggtaaggg ggcatctgtt ggtctgtaga    17460
tgtaaggtcc cctataagtc cctggttgcc accacctgtc tcctattttg acaaaaacac    17520
tcttttttcc cttttttact tctaggcctg tggtcaatag tccttgcacc tgttcttcaa    17580
ttgaggttga gcgtctcttt ctattttcta ttcccatttc taacttctga atttgagtaa    17640
aaatagtact aaaagataat gattcatttc ttaacatagt aactaataat ctacctattg    17700
gattggtctt attggtaaaa atataatttt tagcaagcat tcttatttct atttctgaag    17760
gacaaaatcg atgcggcttg taagaggaag ttggctgtgg tccttgcctc aggaggaagg    17820
tcgagttctc cgaattgttt agattgtaat cttgcacaga agagctatta aaagagtcaa    17880
gggtgagagc cctgcgagca cgaaccgcaa cttcccccaa tagccccagg caaagcagag    17940
ctatgccaag tttgcagcag agaatgaata tgtctttgtc tgatgggctc atccgtttgt    18000
gcgcagacgg gtcgtccttg gtgggaaaca accccttggc tgcttctccc ctaggtgtag    18060
gacactctcg ggagttcaac catttctgcc caagcttggc actggcgcca gaaatccgcg    18120
cggtggtttt tggggtcgg gggtgtttgg cagccacaga cgcccggtgt tcgtgtcgcg    18180
ccagtacatg cggtccatgc ccaggccatc caaaaaccat gggtctgtct gctcagtcca    18240
gtcgtggacc tgaccccacg caacgcccaa aagaataacc cccacgaacc ataaaccatt    18300
ccccatgggg gaccccgtcc ctaacccacg gggcccgtgg ctatgcgggg cttgccgccc    18360
cgacgttggc tgcgagccct gggccttcac ccgaacttgg gggttggggt ggggaaaagg    18420
aagaaacgcg ggcgtattgg ccccaatggg gtctcggtgg ggtatcgaca gagtgccagc    18480
cctgggaccg aaccccgcgt ttatgaacaa acgacccaac acccgtgcgt tttattctgt    18540
cttttttattg ccgtcatagc gcgggttcct tccggtattg tctccttccg tgtttcagtt    18600
agcctccccc atctcccgat ccccacgagt gctggggcgt cggtttccac tatcggcgag    18660
tacttctaca cagccatcgg tccagacggc cgcgcttctg cgggcgattt tgtgtacgcc    18720
gacagtcccg gctccggatc ggacgattgc gtcgcatcga ccctgcgccc aagctgcatc    18780
```

```
atcgaaattg ccgtcaacca agctctgata gagttggtca agaccaatgc ggagcatata   18840
cgcccggagc cgcggcgatc ctgcaagctc cggatgcctc cgctcgaagt agcgcgtctg   18900
ctgctccata caagccaacc acggcctcca gaagaagatg ttggcgacct cgtattggga   18960
atccccgaac atcgcctcgc tccagtcaat gaccgctgtt atgcggccat tgtccgtcag   19020
gacattgttg gagccgaaat ccgcgtgcac gaggtgccgg acttcggggc agtcctcggc   19080
ccaaagcatc agctcatcga gagcctgcgc gacggacgca ctgacggtgt cgtccatcac   19140
agtttgccag tgatacacat ggggatcagc aatcgcgcat atgaaatcac gccatgtagt   19200
gtattgaccg attccttgcg gtccgaatgg gccgaacccg ctcgtctggc taagatcggc   19260
cgcagcgatc gcatccatgg cctccgcgac cggctgcaga acagcgggca gttcggtttc   19320
aggcaggtct tgcaacgtga caccctgtgc acggcgggga atgcaatagg tcaggctctc   19380
gctgaattcc ccaatgtcaa gcacttccgg aatcggagcg cggccgatg caaagtgccg   19440 ataaacataa cgatctttgt agaaaccatc ggcgcagcta tttacccgca ggacatatcc   19500
acgccctcct acatcgaagc tgaaagcacg agattcttcg ccctccgaga gctgcatcag   19560
gtcggagacg ctgtcgaact tttcgatcag aaacttctcg acagacgtcg cggtgagttc   19620 aggcttttc atatctcatt gccccgggg atcttgcggc acgctgttga cgctgttaag   19680
cgggtcgctg cagggtcgct cggtgttcga ggccacacgc gtcaccttaa tatgcgaagt   19740
ggacctggga ccgcgccgcc ccgactgcat ctgcgtgttc gaattcgcca atgacaagac   19800
gctgggcggg gtttgtgtca tcatagaact aaagacatgc aaatatattt cttccgggga   19860
caccgccagc aaacgcgagc aacgggccac ggggatgaag cagcccggcg gcacctcgct   19920
aacggattca ccactccaag aattggagcc aatcaattct tgcggagaac tgtgaatgcg   19980
caaaccaacc cttggcagaa catatccatc gcgtccgcca tctccagcag ccgcacgcgg   20040
cgcatctcgg ggccgacgcg ctgggctacg tcttgctggc gttcgcgacg cgaggctgga   20100
tggccttccc cattatgatt cttctcgctt ccggcggcat cgggatgccc gcgttgcagg   20160
ccatgctgtc caggcaggta gatgacgacc atcagggaca gcttcaagga tcgctcgcgg   20220
ctcttaccag cgccagcaaa aggccaggaa ccgtaaaaag gccgcgttgc tggcgttttt   20280
ccataggctc cgcccccctg acgagcatca caaaaatcga cgctcaagtc agaggtggcg   20340
aaacccgaca ggactataaa gataccaggc gtttccccct ggaagctccc tcgtgcgctc   20400
tcctgttccg accctgccgc ttaccggata cctgtccgcc tttctccctt cgggaagcgt   20460
ggcgctttct catagctcac gctgtaggta tctcagttcg gtgtaggtcg ttcgctccaa   20520
gctgggctgt gtgcacgaac ccccgttca gcccgaccgc tgcgccttat ccggtaacta   20580
tcgtcttgag tccaacccgg taagacacga cttatcgcca ctggcagcag ccactggtaa   20640
caggattagc agagcgaggt atgtaggcgg tgctacagag ttcttgaagt ggtggcctaa   20700
ctacggctac actagaagga cagtatttgg tatctgcgct ctgctgaagc cagttacctt   20760
cggaaaaaga gttggtagct cttgatccgg caaacaaacc accgctggta gcggtggttt   20820
ttttgtttgc aagcagcaga ttacgcgcag aaaaaaagga tctcaagaag atcctttgat   20880
cttttctacg gggtctgacg ctcagtggaa cgaaaactca cgttaaggga ttttggtcat   20940
gagattatca aaaaggatct tcacctagat ccttttaaat taaaaatgaa gttttaaatc   21000
aatctaaagt atatatgagt aaacttggtc tgacagttac caatgcttaa tcagtgaggc   21060
acctatctca gcgatctgtc tatttcgttc atccatagtt gcctgactcc ccgtcgtgta   21120
gataactacg atacgggagg gcttaccatc tggccccagt gctgcaatga taccgcgaga   21180
```

```
cccacgctca ccggctccag atttatcagc aataaaccag ccagccggaa gggccgagcg    21240
cagaagtggt cctgcaactt tatccgcctc catccagtct attaattgtt gccgggaagc    21300
tagagtaagt agttcgccag ttaatagttt gcgcaacgtt gttgccattg ctgcaggcat    21360
cgtggtgtca cgctcgtcgt ttggtatggc ttcattcagc tccggttccc aacgatcaag    21420
gcgagttaca tgatccccca tgttgtgcaa aaaagcggtt agctccttcg gtcctccgat    21480
cgttgtcaga agtaagttgg ccgcagtgtt atcactcatg gttatggcag cactgcataa    21540
ttctcttact gtcatgccat ccgtaagatg cttttctgtg actggtgagt actcaaccaa    21600
gtcattctga gaatagtgta tgcggcgacc gagttgctct tgcccggcgt caacacggga    21660
taataccgcg ccacatagca gaactttaaa agtgctcatc attggaaaac gttcttcggg    21720
gcgaaaactc tcaaggatct taccgctgtt gagatccagt tcgatgtaac ccactcgtgc    21780
acccaactga tcttcagcat cttttacttt caccagcgtt tctgggtgag caaaaacagg    21840
aaggcaaaat gccgcaaaaa agggaataag ggcgacacgg aaatgttgaa tactcatact    21900 cttcctttt caatattatt gaagcattta tcagggttat tgtctcatga gcggatacat    21960
atttgaatgt atttagaaaa ataaacaaat aggggttccg cgcacatttc cccgaaaagt    22020
gccacctgac gtctaagaaa ccattattat catgacatta acctataaaa ataggcgtat    22080
cacgaggccc tttcgtcttc aagaattctc atgtttgaca gcttatcatc gataagctga    22140
tcctcacagg ccgcacccag cttttcttcc gttgccccag tagcatctct gtctggtgac    22200
cttgaagagg aagaggaggg gtcccgagaa tccccatccc taccgtccag caaaaagggg    22260
gacgaggaat ttgaggcctg gcttgaggct caggacgcaa atcttgagga tgttcagcgg    22320
gagttttccg ggctgcgagt aattggtgat gaggacgagg atggttcgga ggatggggaa    22380
ttttcagacc tggatctgtc tgacagcgac catgaagggg atgagggtgg gggggctgtt    22440 ggaggggca ggagtctgca ctccctgtat tcactgagcg tcgtctaata agatgtcta    22500 ttgatctctt ttagtgtgaa tcatgtctga cgaggggcca ggtacaggac ctggaaatgg    22560
cctaggagag aagggagaca catctggacc agaaggctcc ggcggcagtg gacctcaaag    22620 aagaggggt gataaccatg gacgaggacg gggaagagga cgaggacgag gaggcggaag    22680
accaggagcc ccgggcggct caggatcagg gccaagacat agagatggtg tccgagacc    22740 ccaaaaacgt ccaagttgca ttggctgcaa agggacccac ggtggaacag gagcaggagc    22800
aggagcggga ggggcaggag caggaggggc aggagcagga ggaggggcag gagcaggagg    22860
aggggcagga ggggcaggag gggcaggagg ggcaggagca ggaggagggg caggagcagg    22920
aggaggggca ggaggggcag gaggggcagg agcaggagga gggcaggag caggaggagg    22980 ggcaggaggg gcaggagcag gaggaggggc aggaggggca ggaggggcag gagcaggagg    23040
aggggcagga gcaggaggag gggcaggagg ggcaggagca ggaggagggg caggaggggc    23100
aggaggggca ggagcaggag gaggggcagg agcaggaggg gcaggagggg caggaggggc    23160
aggagcagga gggcaggag caggaggagg ggcaggaggg gcaggaggg caggagcagg    23220 aggggcagga gcaggagggg caggagcagg aggggcagga gcaggaggg caggaggggc    23280 aggagcagga ggggcaggag gggcaggagc aggaggggca ggaggggcag gagcaggagg    23340
aggggcagga ggggcaggag caggaggagg ggcaggaggg gcaggagcag gaggggcagg    23400
aggggcagga gcaggagggg caggaggggc aggagcagga ggggcaggag gggcaggagc    23460
aggaggaggg gcaggagcag gaggggcagg agcaggaggt ggaggccggg gtcgaggagg    23520
cagtggaggc cggggtcgag gaggtagtgg aggccggggt cgaggaggta gtggaggccg    23580
```

```
ccggggtaga ggacgtgaaa gagccagggg gggaagtcgt gaaagagcca gggggagagg   23640
tcgtggacgt ggagaaaaga ggcccaggag tcccagtagt cagtcatcat catccgggtc   23700
tccaccgcgc aggcccccctc caggtagaag gccatttttc caccctgtag gggaagccga   23760
ttattttgaa taccaccaag aaggtggccc agatggtgag cctgacgtgc ccccgggagc   23820
gatagagcag ggccccgcag atgacccagg agaaggccca agcactggac cccgggtca    23880 gggtgatgga ggcaggcgca aaaaggagg gtggtttgga aagcatcgtg gtcaaggagg    23940
ttccaacccg aaatttgaga acattgcaga aggtttaaga gctctcctgg ctaggagtca   24000
cgtagaaagg actaccgacg aaggaacttg ggtcgccggt gtgttcgtat atggaggtag   24060
taagacctcc ctttacaacc taaggcgagg aactgcccctt gctattccac aatgtcgtct  24120
tacaccattg agtcgtctcc cctttggaat ggcccctgga cccggccac aacctggccc    24180 gctaagggag tccattgtct gttatttcat ggtctttta caaactcata tatttgctga    24240
ggttttgaag gatgcgatta aggaccttgt tatgacaaag cccgctccta cctgcaatat   24300
cagggtgact gtgtgcagct ttgacgatgg agtagatttg cctccctggt ttccacctat   24360
ggtggaaggg gctgccgcgg agggtgatga cggagatgac ggagatgaag gaggtgatgg   24420
agatgagggt gaggaagggc aggagtgatg taacttgtta ggagacgccc tcaatcgtat   24480
taaaagccgt gtattccccc gcactaaaga ataaatcccc agtagacatc atgcgtgctg   24540
ttggtgtatt tctggccatc tgtcttgtca ccattttcgt cctcccaaca tggggcaatt   24600
gggcataccc atgttgtcac gtcactcagc tccgcgctca acaccttctc gcgttggaaa   24660
acattagcga catttacctg gtgagcaatc agacatgcga cggctttagc ctggcctcct   24720
taaattcacc taagaatggg agcaaccagc aggaaaagga caagcagcga aaattcacgc   24780 cccccttggga ggtggcggca tatgcaaagg atagcactcc cactctacta ctgggtatca   24840
tatgctgact gtatatgcat gaggatagca tatgctaccc ggatacagat taggatagca   24900
tatactaccc agatatagat taggatagca tatgctaccc agatatagat taggatagcc   24960
tatgctaccc agatataaat taggatagca tatactaccc agatatagat taggatagca   25020
tatgctaccc agatatagat taggatagcc tatgctaccc agatatagat taggatagca   25080
tatgctaccc agatatagat taggatagca tatgctatcc agatatttgg gtagtatatg   25140
ctacccagat ataaattagg atagcatata ctaccctaat ctctattagg atagcatatg   25200
ctacccggat acagattagg atagcatata ctacccagat atagattagg atagcatatg   25260
ctacccagat atagattagg atagcctatg ctacccagat ataaattagg atagcatata   25320
ctacccagat atagattagg atagcatatg ctacccagat atagattagg atagcctatg   25380
ctacccagat atagattagg atagcatatg ctatccagat atttgggtag tatatgctac   25440
ccatggcaac attagcccac cgtgctctca gcgacctcgt gaatatgagg accaacaacc   25500
ctgtgcttgg cgctcaggcg caagtgtgtg taatttgtcc tccagatcgc agcaatcgcg   25560
cccctatctt ggcccgccca cctacttatg caggtattcc ccggggtgcc attagtggtt   25620
ttgtgggcaa gtggtttgac cgcagtggtt agcgggtta caatcagcca agttattaca    25680
cccttatttt acagtccaaa accgcagggc ggcgtgtggg ggctgacgcg tgcccccact   25740
ccacaatttc aaaaaaaaga gtggccactt gtctttgttt atgggcccca ttggcgtgga   25800
gccccgttta attttcgggg gtgttagaga caaccagtgg agtccgctgc tgtcggcgtc   25860
cactctcttt cccccttgtta caaatagagt gtaacaacat ggttcacctg tcttggtccc   25920
tgcctgggac acatcttaat aaccccagta tcatattgca ctaggattat gtgttgccca   25980
```

```
tagccataaa ttcgtgtgag atggacatcc agtctttacg gcttgtcccc accccatgga  26040
tttctattgt taaagatatt cagaatgttt cattcctaca ctagtattta ttgcccaagg  26100
ggtttgtgag ggttatattg gtgtcatagc acaatgccac cactgaaccc cccgtccaaa  26160
ttttattctg ggggcgtcac ctgaaacctt gttttcgagc acctcacata caccttactg  26220
ttcacaactc agcagttatt ctattagcta aacgaaggag aatgaagaag caggcgaaga  26280
ttcaggagag ttcactgccc gctccttgat cttcagccac tgcccttgtg actaaaatgg  26340
ttcactaccc tcgtggaatc ctgaccccat gtaaataaaa ccgtgacagc tcatggggtg  26400
ggagatatcg ctgttccttg ggacccttt actaacccta attcgatagc atatgcttcc  26460
cgttgggtaa catatgctat tgaattaggg ttagtctgga tagtatatac tactacccgg  26520
gaagcatatg ctacccgttt agggttaaca agggggcctt ataaacacta ttgctaatgc  26580
cctcttgagg gtccgcttat cggtagctac acaggcccct ctgattgacg ttggtgtagc  26640
ctcccgtagt cttcctgggc ccctgggagg tacatgtccc ccagcattgg tgtaagagct  26700
tcagccaaga gttacacata aaggcaatgt tgtgttgcag tccacagact gcaaagtctg  26760
ctccaggatg aaagccactc agtgttggca aatgtgcaca tccatttata aggatgtcaa  26820
ctacagtcag agaacccctt tgtgtttggt cccccccgt gtcacatgtg aacagggcc   26880 cagttggcaa gttgtaccaa ccaactgaag ggattacatg cactgccccg tgaccaatac  26940
aaaacaaaag cgctcctcgt accagcgaag aagggcaga gatgccgtag tcaggtttag   27000
ttcgtccggc ggcggggat c                                              27021
```

EXPRESSION VECTOR WITH ENHANCED GENE EXPRESSION CAPACITY AND METHOD FOR USING THE SAME

BACKGROUND OF THE INVENTION

1. Field of the Invention

The present invention relates to a novel expression vector which is capable of enhancing gene expression through gene amplification in mammalian cells. The expression vector is organized as an inverted dimer (ID) and comprises, in addition to the gene to be expressed, a nuclear anchoring element and at least one inverted repeat element, preferably two inverted repeat elements. The present invention further relates to a method for enhancing gene expression by transfecting the expression vector to a mammalian cell, preferably a human cell.

2. Description of the Prior Art

A conventional gene expression method is used to express human recombinant proteins in a prokaryotic expression system. Most human recombinant proteins require post- and/or peri-translational modifications such as glycosylation, g-carboxylation, or g-hydroxylation. Therefore, a well-known problem with prokaryotic expression systems is that prokaryotic expression systems do not carry out post- and/or peri-translational modifications as mammalian expression systems do. Proteins requiring post- and/or peri-translational modifications for normal function cannot be expressed properly with prokaryotic expression systems.

Another conventional gene expression method widely used to express said human recombinant proteins is a mammalian expression system. A mammalian expression system uses mammalian cells because of their ability to undergo post-translational modifications and peri-translational modifications.

In particular, a mammalian expression system using Chinese hamster ovary (CHO) cells has become a routine and convenient expression system for expressing biopharmaceutical proteins for therapeutic and diagnostic uses.

A conventional method for enhancing gene expression in mammalian cells comprises a step of amplifying a gene by a step-by-step selection against a concentration-increasing selection agent. An embodiment of the conventional method for enhancing gene expression in mammalian cells uses Chinese hamster ovary (CHO) cells and amplifies a dihydrofolate recuctase (DHFR) gene with a step-by-step selection against methotrexate (MTX). See Omasa, 2002, J. Biosci. Bioeng. 94: 600-605.

However, the step-by-step selection is tedious and time-consuming. The process takes months to complete with cells expressing genes in high levels, and the post-translational modifications in non-human mammalian cells are not identical to that in human cells. Moreover, such conventional gene expression enhancing method with gene amplification has not been widely employed in human cells in the production of biopharmaceutical proteins for therapeutic and diagnostic uses. In general, human proteins generated in human cells should have beneficial properties in comparison with their counterparts produced in non-human systems.

It has been observed that a mismatch repair (MMR) system in human cells strongly suppresses gene amplification. See Lin et al., 2001, Nucleic Acids Res 29, 3304-3310; Chen et al., 2001, Proc Natl Acad Sci USA 98, 13802-13807. Thus gene expression enhanced by gene amplification is strongly suppressed in MMR$^+$ (MMR-normal/MMR-proficient) cells. HCT116 cells are MMR$^-$ (MMR-deficient) due to a mutation in the hMLH1 gene. It is shown that HCT116 cells allow gene expression enhancement by gene amplification. In contrast, HCT116+Ch3 (MMR$^+$ due to introduction of chromosome 3 which carries a wild-type hMLH1 gene) or HCT116+hMLH1 (MMR$^+$ due to introduction of a cDNA which carries a wild-type hMLH1 gene) suppresses a drug resistant gene expression enhanced by gene amplification.

To overcome the shortcomings of the conventional gene expression methods and the conventional method for enhancing gene expression in mammalian cells (especially in human cells), the present invention provides a method to mitigate or obviate the aforementioned problems.

SUMMARY OF THE INVENTION

One aspect of the present invention is to provide an expression vector which comprises at least a gene; a nuclear anchoring element; and at least one inverted repeat (IR) element which comprises two lateral nucleic acid sequences, each being complementary to the other. The expression vector is an episomal vector and is further characterized as being capable of transfecting a mammalian cell. Preferably, the IR element contains a central sequence which is inserted between the two lateral nucleic acid sequences and is different from each of the two lateral nucleic acid sequences. Also preferably, the expression vector contains one IR element, such as pGT02-GFP, and most favorably, two IR elements, such as pGT03-GFP and pGT04-ID. In the case where the expression vector contains two IR elements, these two IR elements can be the same or different.

The gene in the expression vector either encodes a protein or can be transcribed into a non-coding RNA. The protein encoded by the gene includes, but is not limited to, signal peptide, growth factor, hormone, cytokine, chemokine, neuropeptide, antigen, antibody, enzyme, clotting factor, anti-angiogenic factor, pro-angiogenic factor, transport protein, receptor, ligand, regulatory protein, structural protein, reporter protein, transcription factor, ribozyme, fusion protein, and drug-resistance protein. The protein is of natural origin or artificially modified, such as EGFP (i.e., enhanced green fluorescent protein), which is a reporter protein.

The non-coding RNA includes, but is not limited to, tRNA, rRNA, antisense RNA, micro-RNA, and double stranded RNA.

The mammalian cell is preferably a human cell, such as a mismatch repair-deficient (MMR$^-$) cell or a mismatch repair-proficient (MMR$^+$) cell. Examples of the MMR$^-$ cell includes, but is not limited to, HCT116 (hMLH1$^-$) cell or a DLD-1 (hMSH6$^-$) cell. Examples of the MMR$^+$ cell includes, but is not limited to HCT116+ch3 or HCT116+hMLH1 cells.

The nuclear-anchoring element is preferably an EBV (Epstein-Barr Virus) gene encoding an EBV nuclear protein EBNA-1 and an EBV replicon oriP.

The expression vector is capable of enhancing the expression of the gene in the mammalian cells.

Another aspect of the present invention provides an expression vector which is organized as an inverted dimer (ID). The expression vector is a circular nucleic acid molecule having two long nucleic acid sequences separated by two inverted repeat (IR) elements. Each of the two long nucleic acid sequences is complementary to the other, each containing at least a gene and a nuclear anchoring element; each of the two IR elements comprises two lateral nucleic acid sequences; each being complementary to the other. The two IR elements are identical to or different from each other. The ID is an episomal vector.

Finally, the present invention provides a method for expressing a gene in a mammalian cell by transfecting the expression vector to the mammalian cell to produce a transfected cell; culturing the transfected cells to allow the transfected cell to produce a protein which is encoded by the gene; and harvesting the protein from the mammalian cell.

The expression vector is transfected into the mammalian cell by electroporation.

Other objectives, advantages and novel features of the invention will become more apparent from the following detailed description when taken in conjunction with the accompanying drawings.

DETAILED DESCRIPTION OF THE PREFERRED EMBODIMENTS

Definitions

Figure 1A:
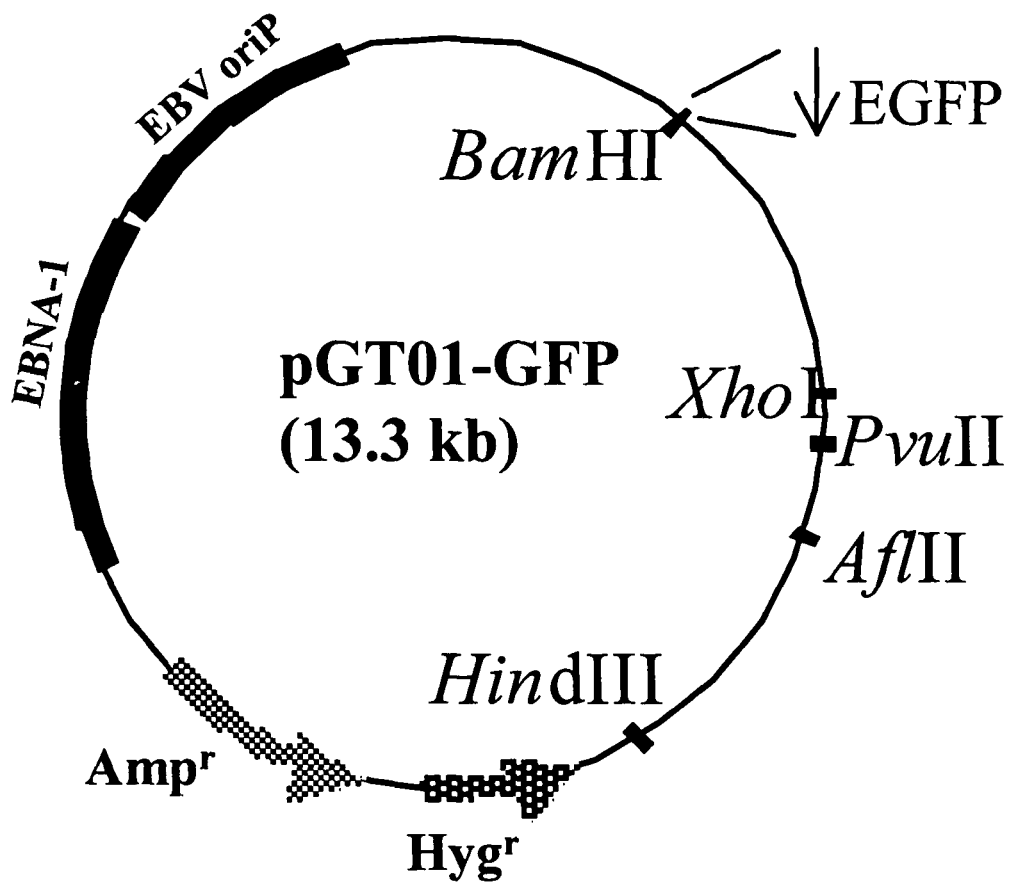
FIG. 1A is a map of an expression vector pGT01-GFP in accordance with the present invention.

The term "expression vector" as used herein, refers to a vector, and in particular, an episomal vector. A vector is generally a plasmid that is used to introduce and express a specific gene into a target cell. The expression vector allows production of large amounts of stable mRNA. Once the expression vector is inside the cell, the protein that is encoded by the gene is produced by the cellular transcription and translation machinery. The plasmid is engineered such that it contains a highly active promoter which causes the production of large amounts of mRNA. An episomal vector is capable of self-replicating autonomously within the host cells.

The term "gene," as used herein, refers to a set of segments of nucleic acid that contains the information necessary to produce a functional RNA product in a controlled manner through a transcription process. This RNA can then be used directly (such as tRNA, rRNA, snRNAs and other non-coding RNAs (e.g., the SRP RNAs), anti-sense RNA, or micro-RNA) or to direct the synthesis of proteins. When the phrase "a gene encoding a protein" or "a protein is encoded by a gene" is used, it means that the gene is transcribed into an mRNA which then is translated into a protein, including post- and peri-translation which occur in the mammalian cells.

Examples of the protein which can be expressed in the mammalian cells via the enhanced replication system of the expression vector includes, but is not limited to, signal peptide, growth factor, hormone, cytokine, chemokine, neuropeptide, antigen, antibody, enzyme, clotting factor, anti-angiogenic factor, pro-angiogenic factor, transport protein, receptor, ligand, regulatory protein, structural protein, reporter gene, transcription factor, ribozyme, fusion protein, and drug-resistance protein. The protein is of natural origin or artificially modified.

The term "reporter gene," as used herein, refers to a "gene" that is attached to another gene of interest in cell culture, animals or plants. Certain genes are chosen as reporters because they are easily identified and measured; or because they are selectable markers. Reporter genes are generally used to determine whether the gene of interest has been taken up by or expressed in the cell or organism population. Commonly used reporter genes include, but is not limited to, the gene that encodes jellyfish green fluorescent protein (GFP), which causes cells that express it to glow green under UV light; the enzyme luciferase, which catalyzes a reaction with a luciferin to produce light; the lacZ gene, which encodes the protein β-galactosidase which causes the host cells expressing the gene to appear blue; and chloramphenicol acetyltransferase (CAT) gene, which confers resistance to the antibiotic chloramphenicol. The protein that is encoded by the reporter gene is called "reporter protein" as used herein The term "reporter gene," as used herein, refers to a "gene" that is attached to another gene of interest in cell culture, animals or plants. Certain genes are chosen as reporters because they are easily identified and measured; or because they are selectable markers. Reporter genes are generally used to determine whether the gene of interest has been taken up by or expressed in the cell or organism population. Commonly used reporter genes include, but is not limited to, the gene that encodes jellyfish green fluorescent protein (GFP), which causes cells that express it to glow green under UV light; the enzyme luciferase, which catalyzes a reaction with a luciferin to produce light; the lacZ gene, which encodes the protein .beta.-galactosidase which causes the host cells expressing the gene to appear blue; and chloramphenicol acetyltransferase (CAT) gene, which confers resistance to the antibiotic chloramphenicol. The protein that is encoded by the reporter gene is called "reporter protein" as used herein The term "inverted repeat element" (hereinafter "IR"), as used herein, refers to a nucleic acid molecule having two lateral nucleic acid sequences and an optional central sequence. Each of the lateral nucleic acid sequences is complementary to the other. The two lateral nucleic acid sequences may form a palindrome. The central sequence is a short nucleic acid sequence different from each of the two lateral nucleic acid sequences, inserted between the two lateral nucleic acid sequences and disrupting the palindrome formed with the two lateral nucleic acid sequences. For example: a nucleic acid having a sequence of "5'-taatccgga tt tccggatta-3'" (SEQ ID NO: 1) wherein the two lateral nucleic acid sequences are "5'-taatccgga-3'" and "5'-tccggatta-3'" while the central sequence is "5'-tt-3'."

Various IRs can be found in many different regions of the human genomes. The human genome IRs information is available to the public. For example, Boston University has an Inverted Repeats Database (IRDB) public repository, which provides information on IRs in genomic DNA and contains a variety of tools for their analysis. See tandem.bu.edu/cgi-bin/ irdb/irdb.exe. These currently include, the Inverted Repeats Finder algorithm, query and filtering capabilities for finding particular repeats of interest, repeat clustering algorithms based on sequence similarity, PCR primer selection, and data download in a variety of formats. In addition, IRDB serves as a centralized research workbench. It provides storage space for results of analysis and permits collaborators to privately share their data and analysis. Other IRs include those described by Lyu, Lin and Liu (Lyu et al., 1999, J. Mol. Biol., 285:1485-1501). IR can also be artificially designed.

The term "inverted dimer"(hereinafter "ID") as used herein, refers to a circular nucleic acid molecule which contains two long nucleic acid sequences separated by two IR elements. Each of the two long nucleic acid sequences is complementary to each other, each containing at least a gene and a nuclear anchoring element. The ID is produced from a linear DNA substrate containing two terminal IRs. Theoretically, the linear DNA substrate containing the two terminal IRs is converted to the dumbbell-like DNA intermediate via proceeding by exonuclease or helicase/nuclease within a cell. Two types of circular IDs can be generated depending on specificity of the exonuclease/helicase. In the first type, a double-stranded 5'→3' or 3'→5' exonuclease can expose the two terminal IRs as protruding single-stranded DNA on opposite DNA strands. Formation of terminal hairpin loops at the inverted repeat sites then converts the DNA into a dumbbell-like intermediate with terminal loops. Subsequent DNA replication converts the dumbbell-like DNA into the circular inverted dimer. In the second type, the same or a different exonuclease/helicase can convert the linear DNA substrate into a single-stranded DNA. This can be achieved by either a single exonuclease or helicase working processively from one end. Annealing the IRs on the single-stranded DNA results in the formation of dumbbell-like DNA with terminal loops. Subsequent DNA replication converts the dumbbell-like DNA into the circular inverted dimer. See Lin et al., 2001, Nucleic Acids Res. 29: 3529-3538, which is herein incorporated by reference.

The term "nuclear anchoring element" refers to a nuclei acid sequence of a nucleic acid molecule that is retained in a nucleus of a cell, especially in a nucleus of a human cell. This nucleic acid molecule, being a vector and having the nuclear anchoring element, anchors to a nuclear matrix of the nucleus. Examples of a nuclear anchoring element includes, but not limited to, an EBV gene encoding an EBV nuclear protein (e.g., nuclear antigen-1 [EBNA-1]) and an EBV origin (i.e., an EBV replicon, oriP); a papovavirus origin of replication and a papovavirus large T antigen; or a polyomavirus (Py) origin (PyOri) and large T (LT) antigen gene (PyLT). See Heffernan and Dennis, 1991, Nucleic Acids Res. 19:85-92).

The preferred nuclear anchoring element is the EBV gene and the EBV origin. It has been shown that the anchoring effect of the EBV gene and the EBV origin is due to a high-affinity matrix attachment of the oriP sequence (Jankelevich et al., 1992, EMBO J., 11, 1165-1176; Mattia et al., 1999, Virology 262, 9-17) and an interaction of oriP with the origin binding protein, EBNA-1 (Lupton and Levine, 1985, Mol. Cell Biol. 5, 2533-2542; Polvino-Bodnar and Schaffer, 1992, Virology 187, 591-603; Yates et al., 1984, Proc. Natl. Acad. Sci. USA 81, 3806-03810).

In accordance with of the present invention, the expression vectors comprising at least one inverted repeat element or organized as an inverted dimer are constructed. These vectors are demonstrated to be selected for increasing gene expression dramatically. When expressing a resistance gene against a selection agent, the cells may be selected with a high concentration selection agent in one step. Proteins expressed by the expression vectors can be obtained rapidly and effectively even in MMR$^+$ human cells.

The method in accordance with the present invention is for producing at least one protein in cells and comprises the following steps of:

(a) preparing an expression vector comprising at least one nuclear anchoring element, at least one gene; and at least one inverted repeat element;

(b) transfecting the expression vector into a mammalian cell to generate a transfected cell;

(c) culturing the transfected cell and allowing the transfected cell to produce a protein which is encoded by the gene; and (d) harvesting the protein.

The preferred mammalian cells to be used in expressing the genes carried by the expression vector include, but are not limited to, Chinese hamster ovarian (CHO) cells, human embryonic kidney (HEK293) cells, human colorectal carcinoma with hMLH1$^{-/-}$ cells (HCT116, HCT116+ch3, and HCT116+hMLH1), human colon cancer cells (DLD-1 (hMSH6$^-$)).

The following experimental designs are illustrative, but not limiting the scope of the present invention. Reasonable variations, such as those occur to reasonable artisan, can be made herein without departing from the scope of the present invention.

EXAMPLE 1

Construction and Transfection of Expression Vectors

With reference to FIG. 1A, a commercially available pEGFP-N1 plasmid (Clontech, Calif.), an EBV-based p220.2 plasmid derived from a commercially available pDR2 plasmid (Clontech, Calif.) and a commercially available pMAMneo plasmid (Clontech, Calif.) were used to construct a pGT01-GFP plasmid.

The pEGFP-N1 plasmid has multiple cloning sites comprising a BglII and a BamHI and an XhoI restriction sites.

The pEGFP-N1 plasmid was digested with BglII and BamHI restriction enzymes to eliminate the XhoI restriction site from the multiple cloning sites and to obtain a linear pEGFP-N1 DNA. The linear pEGFP-N1 DNA underwent self-ligation after agarose gel purification. The elimination of XhoI site was checked with the digestion by EcoRI. An XhoI-eliminated pEGFP-N1 plasmid was obtained. An EGFP gene having an EGFP coding sequence (CDS) encoding an EGFP protein and a CMV promoter driving the EGFP CDS were obtained by the digesting the XhoI-eliminated pEGFP-N1 plasmid with AflII and ApaLI restriction enzymes.

Figure 1B:
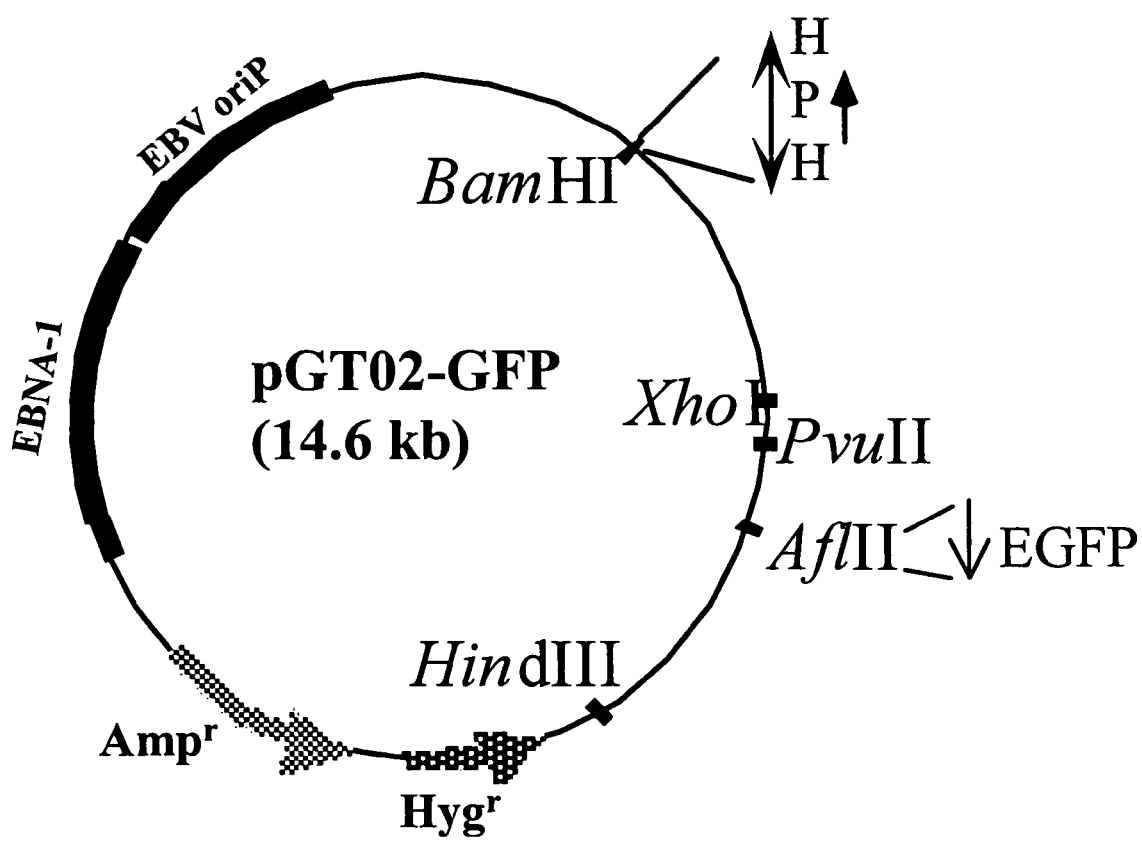
FIG. 1B is a map of an expression vector pGT02-GFP in accordance with the present invention.
Figure 1C:
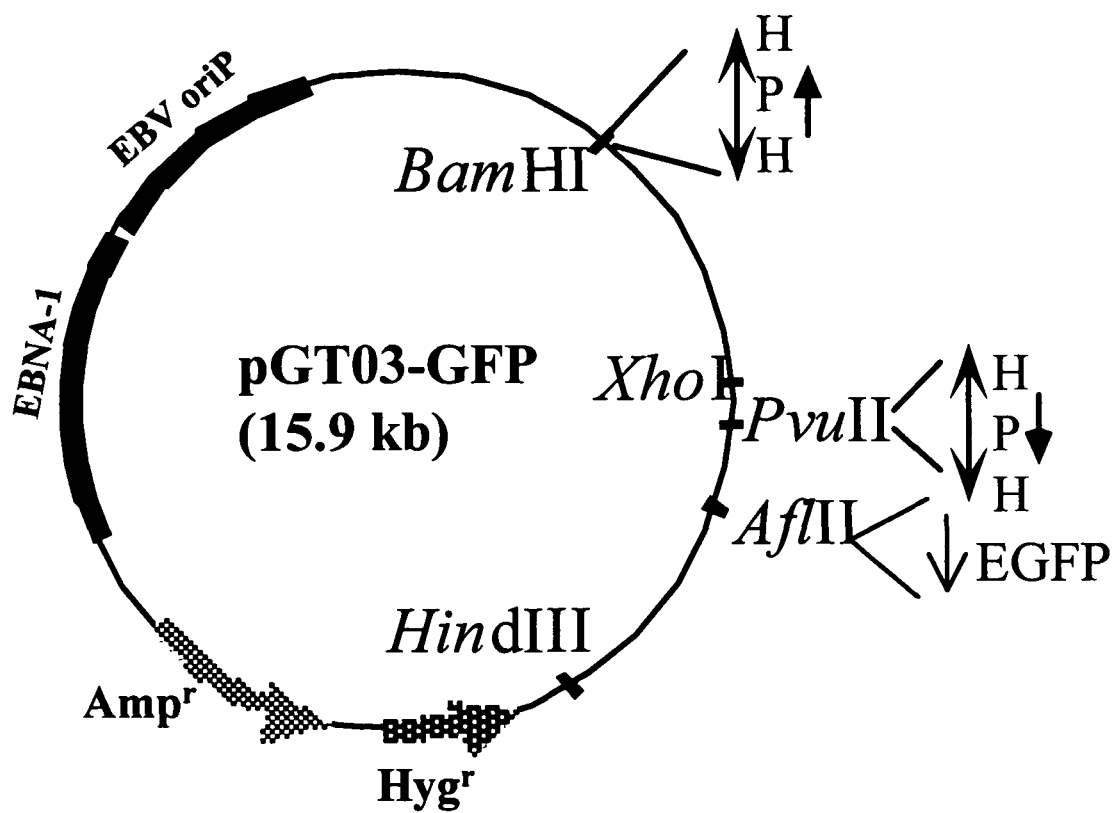
FIG. 1C is a map of an expression vector pGT03-GFP in accordance with the present invention.

With reference to FIGS. 1A, 1B and 1C, a plasmid pGT01-GFP has a nuclear-anchoring element, a gene for hygromycin B resistance, a gene for ampicillin resistance, an HindIII restriction site, an AflII restriction site, a PvuII restriction site, an XhoI restriction site and a BamHI restriction site. The EGFP gene was inserted into the BamHI restriction site as a gene. The nuclear-anchoring element comprises an EBV gene encoding an EBV nuclear protein EBNA-1 and an EBV replicon oriP.

The plasmid, pGT01-GFP, was obtained primarily from the p220.2 plasmid with a BamHI-HindIII fragment of the pMAMneo plasmid.

An HPH fragment, being an inverted repeat element and comprising two H segments as lateral nucleic acid sequences and a P segment as a central sequence of an inverted repeat element, was obtained from a pHPH plasmid. The pHPH plasmid was generated from pBR322 (Bi and Liu, 1996, Proc. Natl. Acad. Sci. USA 93, 819-823). The HPH fragment was formed as an HPH/tet cassette in the pHPH plasmid and was a genetic switch controlling transcription of the functional tetracycline gene, depending on the orientation of the P segment.

The shortened HPH fragment was obtained from a pHPH plasmid (Lin et al., 1997, Nucleic Acids Res. 25, 3009-3016) by NruI digestion.

A plasmid, pGT02-GFP, was generated by cloning the HPH fragment to the blunted BamHI site as a first inverted repeat element and cloning an EGFP gene to the AflII restriction site.

A plasmid, pGT03-GFP, was generated by further cloning the HPH fragment as a second inverted repeat element to the PvuII restriction site of pGT02-GFP in an opposite orientation of P to the first inverted repeat element. The relative orientations of the first inverted repeat element and the second inverted repeat element were determined by restriction enzyme digestion.

Figure 2:
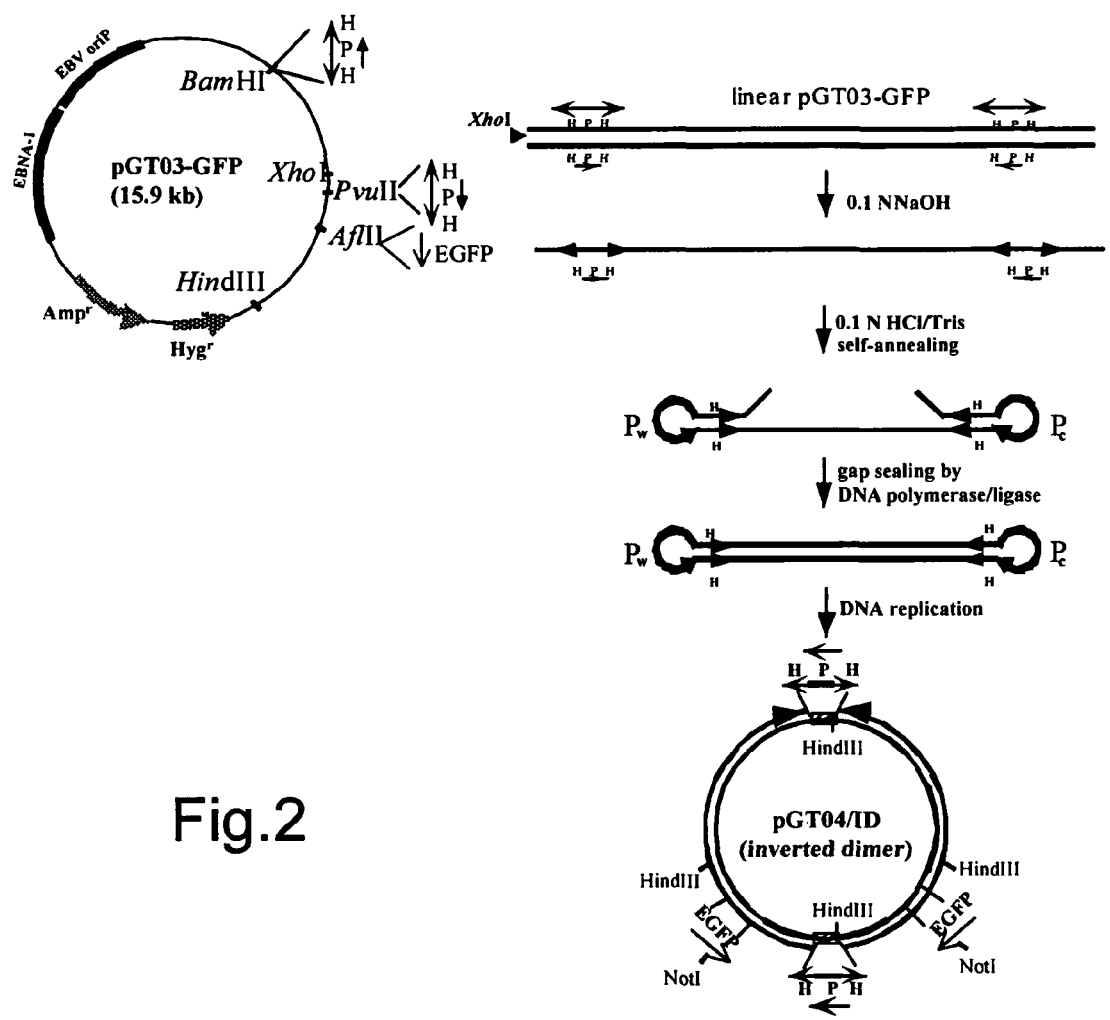
FIG. 2 is a flow chart of generating an expression vector pGT04/ID from the expression vector pGT03-GFP in FIG. 1C.
Figure 3A:
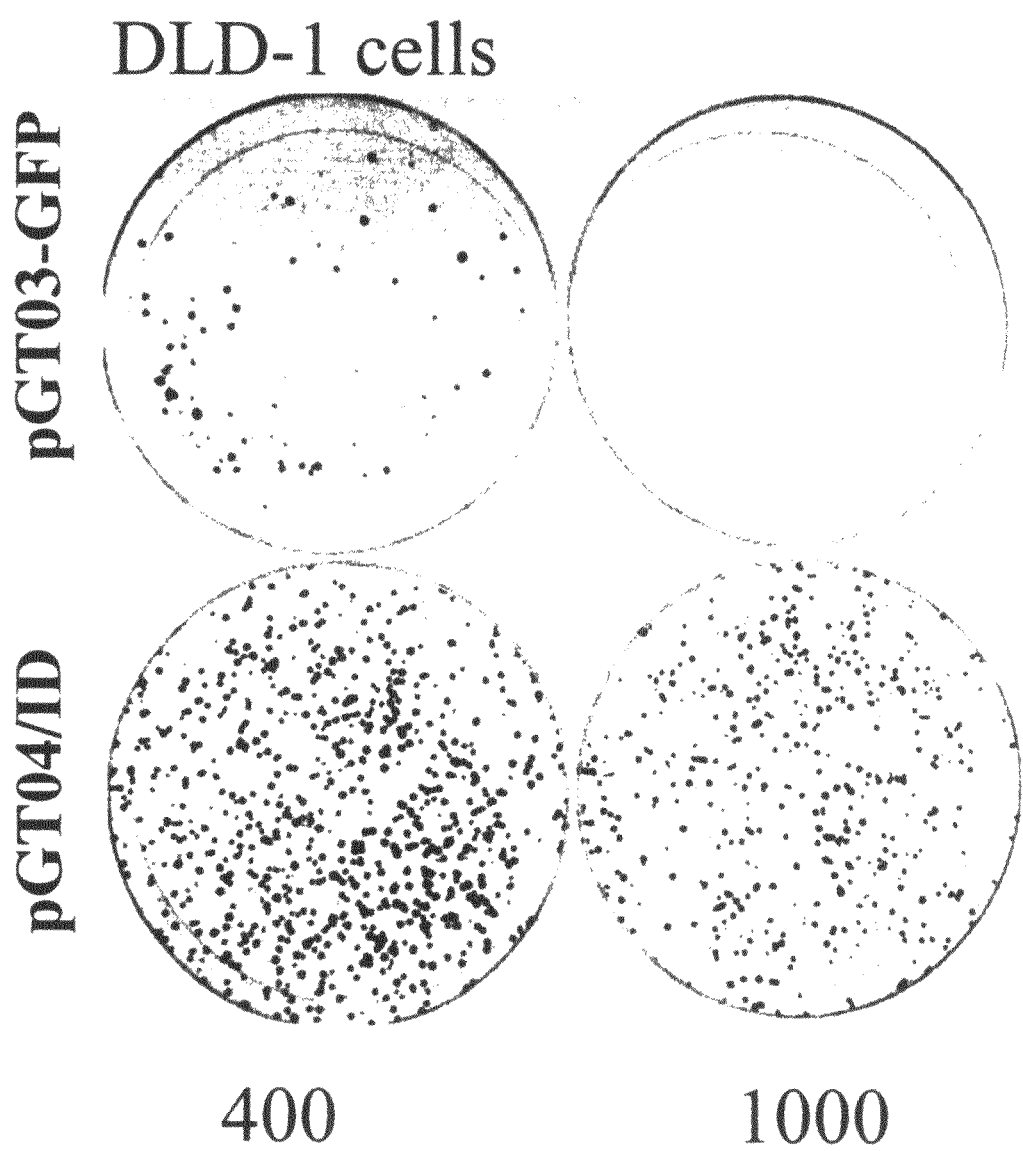
FIG. 3A is a photograph of DLD-1 (hMSH6⁻) cells transfected with pGT03-GFP or pGT04/ID wherein the transfected cells were treated with 400 μg/ml or 1000 μg/ml of hygromycin B.
Figure 3B:
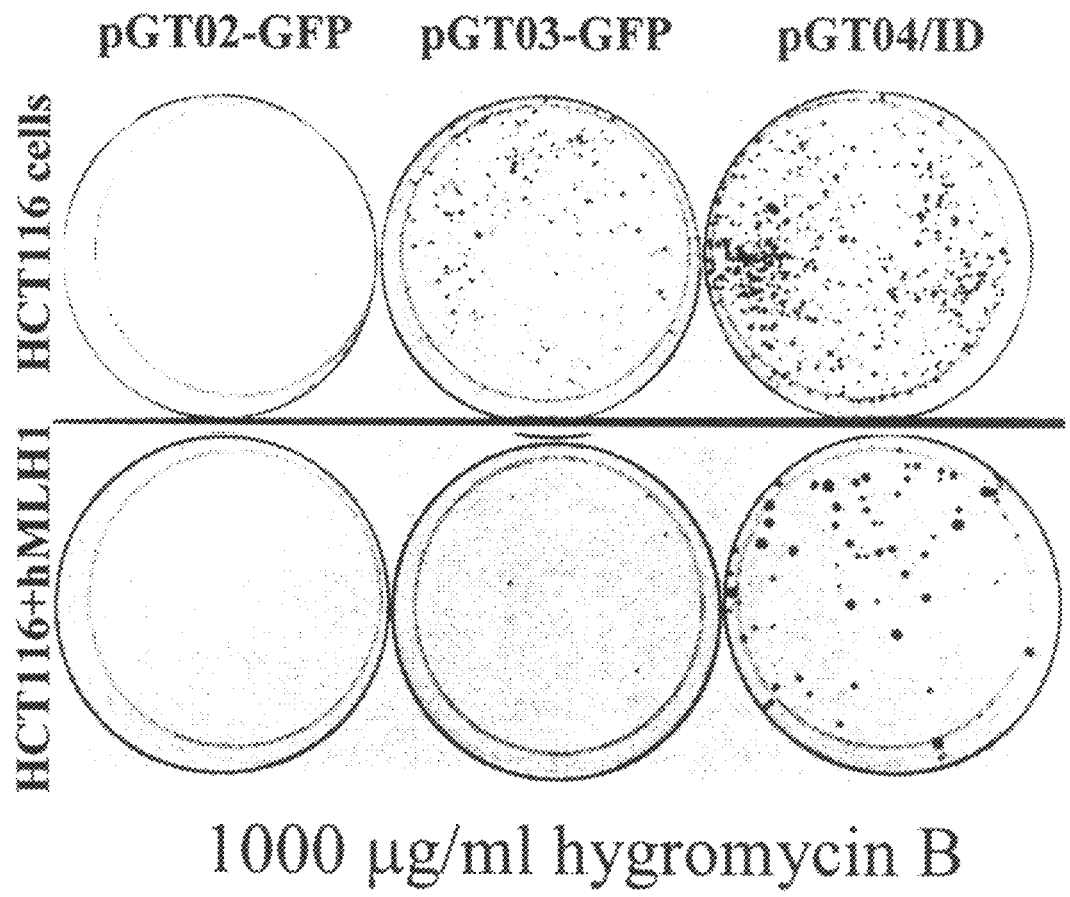
FIG. 3B is a photograph of HCT116 (hMLH1⁻) cells or HCT116+hMLH1 cells transfected with pGT02-GFP, pGT03-GFP or pGT04/ID wherein the transfected cells were treated with 1000 μg/ml of hygromycin B.
Figure 3C:
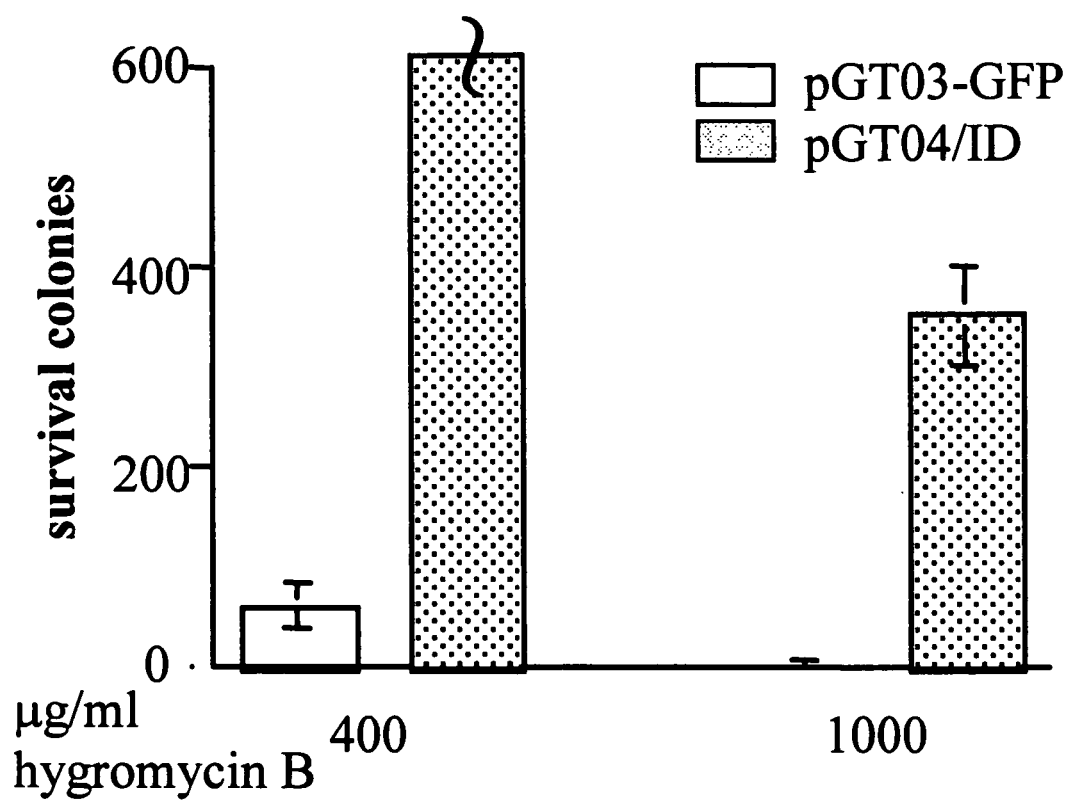
FIG. 3C is a bar chart showing the survival colonies of the transfected cells in FIG. 3A.
Figure 3D:
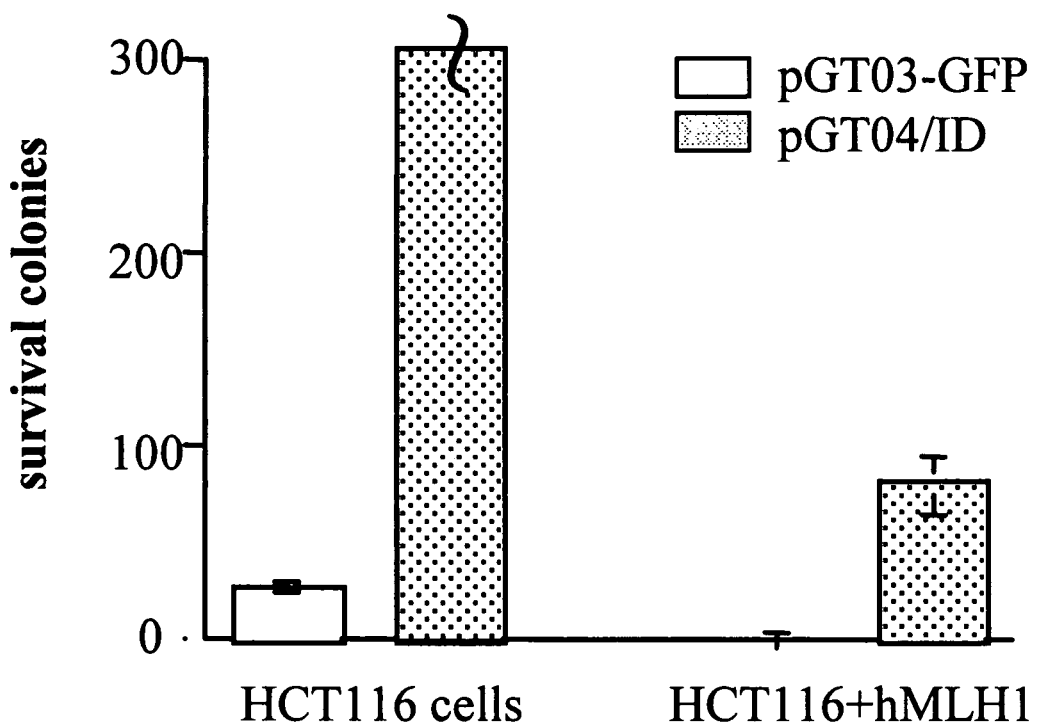
FIG. 3D is a bar chart showing the survival colonies of the cells transfected with pGT03-GFP or pGT04/ID in FIG. 3B.

With further reference to FIG. 2, pGT03-GFP was digested with XhoI enzyme and undergone gel-purification to obtain a linear pGT03-GFP DNA.

The linear pGT03-GFP DNA has two ends and the first inverted repeat element and the second repeat were respectively located near the ends.

The linear pGT03-GFP DNA was denatured to obtain a neutralized DNA solution containing a single stranded linear pGT03-GFP DNA. The denaturation of the linear pGT03-GFP DNA was achieved by alkali denaturation with a volume of 0.1 N NaOH.

An equal volume of 0.1 N HCl plus one tenth volume of 1 M Tris (pH 7.8) was added to the neutralized and thereby quench the DNA solution. The neutralized DNA solution was briefly incubated at 37° C. for 10 min and then kept on ice.

Each of the lateral nucleic acid sequences (H segments) of the first inverted repeat element was allowed to be annealed to the other; and so was each of the lateral nucleic acid sequences of the second repeat.

A hairpin-like structure was formed near each of the two ends of the single stranded linear pGT03-GFP DNA to obtain a self-annealing single stranded linear pGT03-GFP DNA. With reference to FIG. 2, a gap was formed between the ends of the self-annealing single stranded linear pGT03-GFP DNA. A DNA polymerase and a ligase may be employed to treat the a self-annealing single stranded linear pGT03-GFP DNA to seal the gap and to obtain a dumbbell-like DNA (Lin et al., 1997, Nucleic Acids Res. 25, 3009-3016; Lin et al., 2001, Nucleic Acids Res. 29: 3529-3538).

The self-annealing single stranded linear pGT03-GFP DNA was introduced into an *E. coli* DH5α (RecA$^-$) to allow DNA replication and to generate a double stranded DNA plasmid pGT04/ID (SEQ ID NO: 2) from the dumbbell-like DNA as shown in FIG. 2.

The constructed pGT01-GFP, pGT02-GFP, pGT03-GFP and pGT04/ID, being used as expression vectors, were used to transfect into cells by electroporation using a commercially available Nuleofector system (Amaxa, Germany) according to the manufacturer's instructions. Transfected cells were cultured for 24-48 hours before addition of 50 μg/ml of hygromycin B for selecting stable clones.

The main objective in accordance with the present invention was to enhance the gene expression in transfected cells. To this end, the expression vectors capable of replicating in human cells was designed to allow for the persistence of molecules over prolonged periods of culture by containing the nuclear-anchoring element. In the example, the nuclear-anchoring element comprises the EBNA-1 and the oriP. A vector or an expression vector containing EBNA-1 and oriP is also known as an EBV vector. It has been shown that EBV vectors anchor to the nuclear matrix through a high-affinity matrix attachment region containing the oriP sequence (Jankelevich et al., 1992, EMBO J., 11, 1165-1176; Mattia et al., 1999, Virology, 262, 9-17). Furthermore, interaction of oriP with the origin binding protein, EBNA-1 is required for EBV vector replication, segregation, and retention in primate cells (Lupton and Levine, 1985, Mol. Cell. Biol. 5, 2533-2542; Polyino-Bodnar and Schaffer, 1992, Virology 187, 591-603; Yates et al., 1984, Proc. Natl. Acad. Sci. USA 81, 3806-3810). With further reference to FIGS. 1A, 1B and 1C, to demonstrate whether the DNA rearrangement mediated by at least one inverted repeat element can further enhance the gene expression through the increased drug selection and the gene copies, the expression vectors containing EBV elements and at least one inverted repeat (IR) element were constructed as described above. The EGFP gene encoding an EGFP protein driven by a CMV promoter was cloned into each of the expression vectors as a gene. With further reference to FIG. 2, the inverted dimer, pGT04/ID, was generated from pGT03-GFP through an IR-mediated rearrangement.

EXAMPLE 2

Preparation of Cells

HCT116 (human colorectal carcinoma with hMLH1$^{-/-}$) cells were obtained from Dr. C. R. Boland (UCSD, Calif.) (Koi et al., 1994, Cancer Res. 54, 4308-4312; ATCC#CCL-247).

Plasmid pC9MLHWT harboring the wild-type hMLH1 cDNA (under the control of CMV promoter) were obtained from Dr. B. Vogelstein.

Plasmid pC9MLHWT was used to transfect HCT116 cells by electroporation to restore the mismatch repair function (Lin et al., Nucleic Acids Res. 29, 3304-3310). The resulting G418-resistant clone expressing the hMLH1 protein was termed HCT116+hMLH1. HCT116+hMLH1 cells were cultured in the presence of 100 μg/ml of G418.

Another colon cancer cell line DLD-1 (hMSH6$^-$) (ATCC#CCL-221) was obtained from Dr. Thomas A. Kunkel (NIEHS, NC). DLD-1 cells were cultured in complete RPMI medium supplemented with 10% fetal bovine serum.

EXAMPLE 3

Enrichment Assay

About 1×10$^4$ of subconfluent cells were seeded in 100×20 mm culture dishes with complete RPMI-1640 or DMEM medium supplemented with 10% commercially available fetal bovine serum (Gibco) 24 hrs prior to drug selection. As nutrition of the medium consumed and cell wastes accumulated, the aged medium was renewed in a period of time with a fresh medium. Following medium renewal, hygromycin B was added in indicated concentrations to each plate. The culture dishes were incubated in a 37° C. incubator supplied with 5% CO$_2$. Depending on the cytotoxicity induced by the hygromycin B, cells were replenished with fresh medium after treatment for 2 to 4 days. Survival colonies were observed after 10-14 days of growth. The plating efficiency of cell lines was determined by seeding 500 cells in a 100×20 mm culture dish and counting the colonies after 10 days of growth.

EXAMPLE 4

(1) Measurement of Enhanced Green Fluorescence Protein (EGFP) Production

Cells were washed once with PBS, trypsinized, and resuspended in PBS. The green fluorescence of EGFP was measured at an excitation wavelength of 480 nm and an emission wavelength of 525 nm using a FACS Vantage cell sorter (Becton Dickinson, Mountain View, Calif.).

(2) Enhanced Recombinant Gene Expression

The human colon cancer cells, DLD-1, HCT116, and HCT116+hMLH1, were transfected with each of the expression vectors and selected for stable clones with 50 μg/ml of hygromycin B. Multiple stable clonal cells of each stable clone were cultured. $1 \times 10^4$ stable clonal cells of each human colon cancer cells were seeded and further cultured in medium containing either 400 μg/ml or 1000 μg/ml of hygromycin B.

Figure 4A:
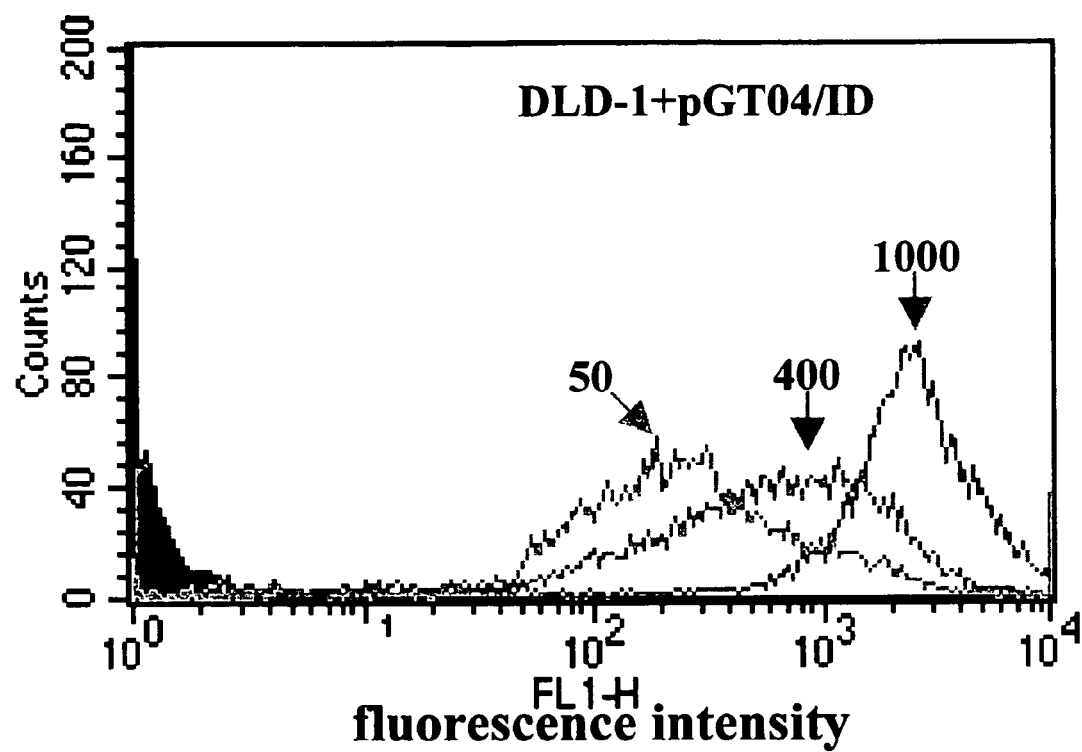
FIG. 4A is a graph of cell counts versus green fluorescence intensity of DLD-1 cells transfected with pGT04/ID and treated with 50 μg/ml, 400 μg/ml or 1000 μg/ml of hygromycin B.

With further reference to FIGS. 3A, 3B, 3C and 3D, colon cancer cell lines, DLD-1 (MMR⁻) and HCT116 (MMR⁻) cells, transfected with pGT04/ID gave rise to over 50 times more colonies than cells with at least one inverted repeat element upon selection with 1000 μg/ml of hygromycin B. With further reference to FIG. 4A, the increased yields of EGFP were observed in cells upon culture in 400 μg/ml or 1000 μg/ml of hygromycin B by flow cytometry.

EXAMPLE 5

Western Blotting

A cocktail of protease inhibitors is a mixture of protease inhibitors with broad specificity for the inhibition of proteases such as serine, cysteine, aspartic proteases and aminopeptidases. A cocktail of protease inhibitors may contain 4-(2-aminoethyl)benzenesulfonyl fluoride (AEBSF), pepstatinA, E-64, bestatin, leupeptin, and aprotinin. A cocktail of protease inhibitors may contain no metal chelators. A cocktail of protease inhibitors may be commercially available.

Cell extracts were prepared in lysis buffer (50 mM HEPES pH 7.6, 0.5% SDS, 1% sodium deoxycholate and 5 mM EDTA) containing a cocktail of protease inhibitors (Sigma). Same amounts of protein samples were separated on 12% SDS-PAGE gel and electroblotted to polyvinylidene fluoride membranes (Amersham). An antibody against GFP (Chemicon International) and an antibody against actin (1-19; Santa Cruz Biotechnology) were used to carry out Western-blotting. Secondary antibodies conjugated with horseradish peroxidase (Sigma) and enhanced chemiluminescence (ECL; Amersham) were used for detection.

Figure 4B:
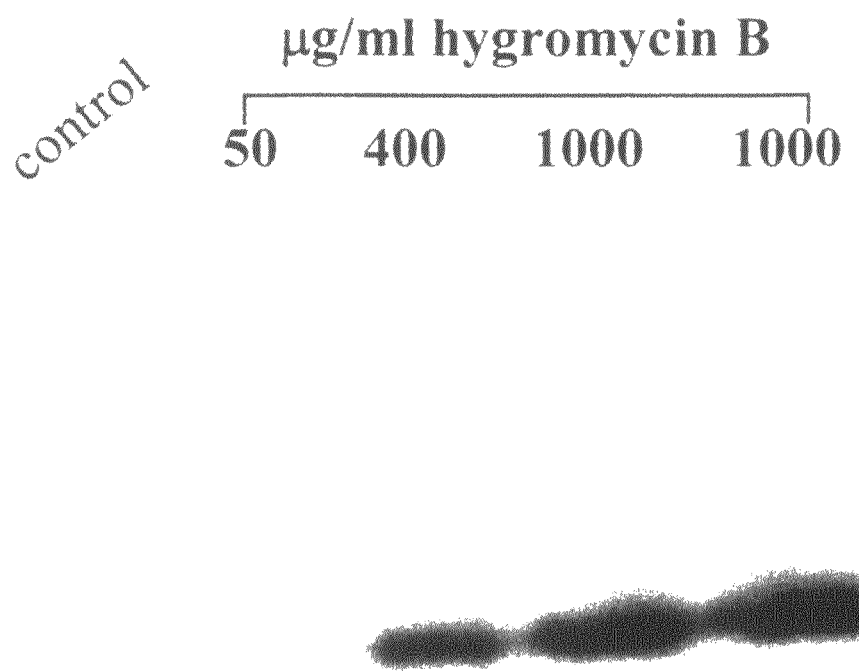
FIG. 4B is a photograph of a Western-blotting analysis of EGFP expression of the cells in FIG. 4A. Non-transfected DLD-1 cells were used as negative control. Control of protein loading level was performed with anti-actin monoclonal antibody in the gel of cell extracts (data not shown).

With further reference to FIG. 4B, the increased yields of EGFP was observed in cells upon culture in 50 μg/ml, 400 μg/ml or 1000 μg/ml of hygromycin B by Western blotting.

RESULTS

The examples shown above clearly demonstrated that the expression vector containing both the nuclear anchoring element and the IR element(s) enhanced the transgene expression of genes in both MMR⁻ and MMR⁺ cells.

The experiments of the present invention were carried out by transfecting an expression vector containing a nuclear anchoring element, one or two IR elements, two drug-resistance genes (i.e., hygromycin B-resistance gene and an ampicillin gene) and a reporter gene (i.e., an EGFP gene) to the human cells. As shown in FIG. 3, the transfected cells demonstrated a drastic improvement in drug-resistance (i.e., hygromycin B-resistance), as demonstrated by the finding that more clones survived in 1000 μg of hygromycin B. Also, as shown in FIG. 4, the concentration of EGFP in the clones that survived in higher concentration of hygromycin B was significantly higher than those survived in lower concentration of hygromycin B and in the control (which was not transfected by the expression vector), as demonstrated by the elevated intensity of fluorescence and the higher staining of EGFP in SDS-polyacrylamide gel electrophoresis. This result confirmed that the gene amplification and expression was enhanced in the transfected cells. Most significantly, the improvement was not only found in MMR-deficient cells (which did not suppress gene amplification and expression), but also in MMR-proficient cells (which should have the effect of suppressing gene amplification and expression).

Among the various vectors constructed in the present invention, the pGT04/ID expression vector structured as the circular inverted dimer ("ID") provided the highest drug-resistance effect and EGFP concentration in the host cells.

A skilled artisan would understand that the drug-resistance genes and EGFP gene as used herein can be replaced with a gene encoding other proteins, such as growth factors, hormones, cytokines, chemokines, neuropeptides, antigens, antibodies, enzymes, clotting factors, anti-angiogenic factors, pro-angiogenic factors, transport proteins, receptors, ligands, regulatory proteins, structural proteins, transcription factors, and ribozymes. Therefore, the present invention has demonstrated that the expression vector can be used for large production of therapeutic proteins and for screening the best expression systems or cell lines for protein production.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. An isolated, circular, double-stranded, inverted dimer (ID) expression vector, consisting of:
   a first inverted repeat (IR) element having a first end and a second end; a second IR element having a first end and a second end;
   a first sequence located between said first end of said first IR element and said first end of said second IR element; and
   a second sequence located between said second end of said first IR element and said second end of said second IR element,
   wherein said first sequence and said second sequence are fully complementary to each other, each of said first and second sequences comprising a nuclear anchoring element and at least a gene,
   wherein each of said first and second IR elements comprises two lateral nucleic acid sequences, each being complementary to the other, and a central sequence that is different from each of said two lateral nucleic acid sequences,
   wherein said expression vector is organized as an inverted dimer (ID) for enhancing gene expression in mammalian cells,
   wherein said expression vector is capable of transfecting mammalian cells,
   wherein said expression vector is an episomal vector in transfected mammalian cells,
   wherein said expression vector comprises pGT04-ID, and
   wherein said gene encodes a protein which is selected from the group consisting of signal peptide, growth factor, hormone, cytokine, chemokine, neuropeptide, antigen, antibody, enzyme, clotting factor, anti-angiogenic factor, pro-angiogenic factor, transport protein, receptor, ligand, regulatory protein, structural protein, reporter protein, transcription factor, ribozyme, fusion protein, and drug-resistance protein.

2. The expression vector according to claim 1, wherein said protein is of natural origin or artificially modified.

3. The expression vector according to claim 2, wherein said reporter protein is an enhanced green fluorescent protein (EGFP).

4. The expression vector according to claim 1, wherein said gene is transcribed into an RNA which is one selected from the group consisting of tRNA, rRNA, antisense RNA, microRNA, and double stranded RNA.

5. The expression vector according to claim 1, wherein said mammalian cells are Chinese hamster ovary (CHO) cells.

6. The expression vector according to claim 1, wherein said mammalian cells are human cells.

7. The expression vector according to claim 6, wherein said human cells are mismatch repair-deficient (MMR$^-$) cells.

8. The expression vector according to claim 7, wherein said MMR$^-$ cells are HCT116 (hMLH1$^-$) cells or DLD-1 (hMSH6$^-$) cells.

9. The expression vector according to claim 6, wherein said human cells are mismatch repair-proficient (MMR$^+$) cells.

10. The expression vector according to claim 1, wherein the nuclear-anchoring element comprises an EBV (Epstein-Barr Virus) gene encoding an EBV nuclear protein EBNA-1 and an EBV replicon oriP.

11. A pGT04-ID expression vector comprising a gene selected from the group consisting of signal peptide, growth factor, hormone, cytokine, chemokine, neuropeptide, antigen, antibody, enzyme, clotting factor, anti-angiogenic factor, pro-angiogenic factor, transport protein, receptor, ligand, regulatory protein, structural protein, reporter protein, transcription factor, ribozyme, fusion protein, and drug-resistance protein.

12. The expression vector according to claim 1, wherein said expression vector is capable of enhancing expression of said gene in said mammalian cells.

13. An in vitro human cell comprising the expression vector according to claim 1.

14. The human cell according to claim 13, wherein said human cell is a mismatch repair-deficient (MMR$^-$) cell.

15. The human cell according to claim 13, wherein said human cell is a mismatch repair-proficient (MMR$^+$) cell.

16. A CHO cell comprising the expression vector according to claim 1.

17. The CHO cell according to claim 16, wherein said CHO cell is a mismatch repair-deficient (MMR$^-$) cell.

18. The CHO cell according to claim 16, wherein said CHO cell is a mismatch repair-proficient (MMR$^+$) cell.

19. A method for expressing a gene in a mammalian cell comprising:
   transfecting the expression vector according to claim 1 into a mammalian cell in vitro to produce a transfected cell;
   culturing said transfected cell to allow said transfected cell to produce a protein which is encoded by said gene; and
   harvesting said protein from said cultured transfected cell.

20. The method according to claim 19, wherein said gene is transcribed into an RNA which is one selected from the group consisting of tRNA, rRNA, antisense RNA, micro-RNA, and double stranded RNA.

21. The method according to claim 19, wherein said mammalian cell is a human cell.

22. The method according to claim 21, wherein said human cell is a mismatch repair-deficient (MMR$^-$) cell.

23. The method according to claim 22, wherein said MMR$^-$ cell is a HCT116 (hMLH1$^-$) cell or a DLD-1 (hMSH6$^-$) cell.

24. The method according to claim 21, wherein said human cell is a mismatch repair-proficient (MMR$^+$) cell.

25. The method according to claim 19, wherein said mammalian cell is a CHO cell.

26. The method according to claim 25, wherein said CHO cell is a mismatch repair-deficient (MMR$^-$) cell.

27. The method according to claim 25, wherein said CHO cell is a mismatch repair-proficient (MMR$^+$) cell.

* * * * *